(12) United States Patent
Ohsawa et al.

(10) Patent No.: US 8,349,533 B2
(45) Date of Patent: *Jan. 8, 2013

(54) RESIST LOWER-LAYER COMPOSITION CONTAINING THERMAL ACID GENERATOR, RESIST LOWER LAYER FILM-FORMED SUBSTRATE, AND PATTERNING PROCESS

(75) Inventors: Youichi Ohsawa, Jyoetsu (JP); Jun Hatakeyama, Jyoetsu (JP); Takeru Watanabe, Jyoetsu (JP); Takeshi Kinsho, Jyoetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 468 days.

This patent is subject to a terminal disclaimer.

(21) Appl. No.: 12/588,590

(22) Filed: Oct. 20, 2009

(65) Prior Publication Data

US 2010/0119970 A1    May 13, 2010

(30) Foreign Application Priority Data

Nov. 7, 2008 (JP) .................................. 2008-286593

(51) Int. Cl.
G03F 7/028    (2006.01)
G03F 7/029    (2006.01)

(52) U.S. Cl. ..................... 430/270.1; 430/919; 430/920; 430/923; 430/925; 430/927

(58) Field of Classification Search ............... 430/270.1, 430/271.1, 919, 920, 923, 925, 927
See application file for complete search history.

(56) References Cited

U.S. PATENT DOCUMENTS

| | | | |
|---|---|---|---|
| 5,348,838 A * | 9/1994 | Ushirogouchi et al. ... | 430/270.1 |
| 5,585,507 A | 12/1996 | Nakano et al. | |
| 5,650,483 A | 7/1997 | Malik et al. | |
| 5,705,702 A | 1/1998 | Osawa et al. | |
| 5,714,625 A | 2/1998 | Hada et al. | |
| 5,886,119 A | 3/1999 | Schaedeli et al. | |
| 5,902,713 A | 5/1999 | Hada et al. | |
| 5,972,560 A | 10/1999 | Kaneko et al. | |
| 6,261,738 B1 | 7/2001 | Asakura et al. | |
| 6,309,796 B1 | 10/2001 | Nakashima et al. | |
| 6,420,088 B1 | 7/2002 | Angelopoulos et al. | |
| 6,440,634 B1 | 8/2002 | Ohsawa et al. | |
| 6,506,497 B1 | 1/2003 | Kennedy et al. | |
| 6,620,957 B1 | 9/2003 | Tomita et al. | |
| 6,623,907 B2 * | 9/2003 | Numata et al. ............ | 430/270.1 |
| 6,723,483 B1 | 4/2004 | Oono et al. | |
| 6,730,453 B2 * | 5/2004 | Nakashima et al. ....... | 430/270.1 |
| 2001/0012596 A1 | 8/2001 | Kunimoto et al. | |
| 2001/0033990 A1 * | 10/2001 | Hatakeyama et al. ..... | 430/270.1 |
| 2001/0036591 A1 | 11/2001 | Schulz et al. | |
| 2002/0012871 A1 | 1/2002 | Hatakeyama et al. | |
| 2002/0102491 A1 | 8/2002 | Kodama et al. | |
| 2003/0008237 A1 | 1/2003 | Pavelchek et al. | |
| 2004/0191479 A1 | 9/2004 | Hatakeyama et al. | |
| 2004/0241577 A1 | 12/2004 | Hatakeyama et al. | |
| 2004/0247900 A1 | 12/2004 | Ogihara et al. | |
| 2005/0074695 A1 | 4/2005 | Nakamura et al. | |
| 2005/0277058 A1 | 12/2005 | Iwabuchi et al. | |
| 2006/0014106 A1 | 1/2006 | Hatakeyama et al. | |
| 2006/0019195 A1 | 1/2006 | Hatakeyama et al. | |
| 2006/0021964 A1 | 2/2006 | Hirayama et al. | |
| 2006/0068335 A1 | 3/2006 | Coley et al. | |
| 2006/0073413 A1 | 4/2006 | Takemura et al. | |
| 2006/0204891 A1 | 9/2006 | Hatakeyama et al. | |
| 2006/0228648 A1 | 10/2006 | Ohsawa et al. | |
| 2006/0234158 A1 | 10/2006 | Hatakeyama | |
| 2007/0023288 A1 * | 2/2007 | Kuwano et al. ............... | 204/486 |
| 2007/0105990 A1 | 5/2007 | Makino et al. | |
| 2007/0117044 A1 | 5/2007 | Ogihara et al. | |
| 2007/0122740 A1 * | 5/2007 | Hatakeyama et al. ..... | 430/270.1 |
| 2007/0134916 A1 | 6/2007 | Iwabuchi et al. | |
| 2007/0172759 A1 | 7/2007 | Ogihara et al. | |
| 2007/0275325 A1 | 11/2007 | Hatakeyama et al. | |
| 2008/0011987 A1 | 1/2008 | Arao et al. | |
| 2008/0020290 A1 * | 1/2008 | Hatakeyama et al. ............ | 430/4 |
| 2008/0032231 A1 * | 2/2008 | Hatakeyama et al. ..... | 430/270.1 |
| 2008/0038662 A1 | 2/2008 | Hatakeyama et al. | |
| 2008/0153030 A1 * | 6/2008 | Kobayashi et al. ........ | 430/270.1 |
| 2008/0311514 A1 | 12/2008 | Nakashima et al. | |
| 2009/0042128 A1 * | 2/2009 | Takemoto .................. | 430/281.1 |
| 2009/0104559 A1 * | 4/2009 | Houlihan et al. .......... | 430/270.1 |
| 2009/0234155 A1 * | 9/2009 | Oh et al. ........................ | 562/100 |

(Continued)

FOREIGN PATENT DOCUMENTS

CA        2049772        2/1992

(Continued)

OTHER PUBLICATIONS

Moran et al., "High Resolution, Steep Profile Resist Patterns," *J Vac. Sci. Techonolo*, vol. 16, No. 1, pp. 1620-1624, 1979.
Brunsvold et al., "Evaluation of a Deep UV Bilayer Resist for Sub-Half Micron Lithography," *SPIE*, vol. 1925, pp. 377-387, 1993.
Hatakeyama et al., "Investigation of Discrimination Enhancement in Polysilsesquioxane Based Positive Resist for ArF Lithography," *SPIE*, vol. 3333, pp. 63-72, 1998.
DeVoe et al., "Photochemistry and Photophysics of 'Onium Salts'," *Advances in Photochemistry*, vol. 17, pp. 1313-1355, 1992.
Miller et al., "Deoxygenation of Sulfoxides Promoted by Electrophilic Silicon Reagents: Preparation of Aryl-Substituted Sulfonium Salts," *American Chemical Society*, pp. 5571-5573, 1988.
Lowe, "Synthesis of Sulphonium Salts," The Chemistry of the Sulphonium Group, Chapter 11, pp. 267-312, 1981.

(Continued)

*Primary Examiner* — Anca Eoff
(74) *Attorney, Agent, or Firm* — Oliff & Berridge, PLC

(57) ABSTRACT

A resist lower-layer composition configured to be used by a multi-layer resist method used in lithography to form a layer lower than a photoresist layer acting as a resist upper layer film. The resist lower-layer composition is insoluble or poorly-soluble in an alkaline developer after formation of the lower layer, and the resist lower-layer composition comprises, at least, a thermal acid generator for generating an acid by heating at a temperature of 100° C. or higher.

8 Claims, 10 Drawing Sheets

U.S. PATENT DOCUMENTS

| | | | |
|---|---|---|---|
| 2009/0246694 A1* | 10/2009 | Ohsawa et al. | 430/285.1 |
| 2010/0035185 A1* | 2/2010 | Hagiwara et al. | 430/286.1 |
| 2011/0034721 A1* | 2/2011 | Hagiwara et al. | 560/117 |

FOREIGN PATENT DOCUMENTS

| | | |
|---|---|---|
| JP | A-4-230645 | 8/1992 |
| JP | A-5-267158 | 10/1993 |
| JP | A-5-291130 | 11/1993 |
| JP | A-6-118651 | 4/1994 |
| JP | A-7-25846 | 1/1995 |
| JP | A-8-311018 | 11/1996 |
| JP | A-9-15848 | 1/1997 |
| JP | A-9-95479 | 4/1997 |
| JP | A-9-110938 | 4/1997 |
| JP | A-9-208554 | 8/1997 |
| JP | A-9-230588 | 9/1997 |
| JP | A-9-301948 | 11/1997 |
| JP | A-10-324748 | 12/1998 |
| JP | B2-2906999 | 4/1999 |
| JP | A-11-302382 | 11/1999 |
| JP | A-2000-314956 | 11/2000 |
| JP | A-2001-122850 | 5/2001 |
| JP | A-2001-181221 | 7/2001 |
| JP | A-2001-233842 | 8/2001 |
| JP | A-2002-55456 | 2/2002 |
| JP | A-2002-167340 | 6/2002 |
| JP | A-2002-193887 | 7/2002 |
| JP | A-2002-193925 | 7/2002 |
| JP | A-2003-114533 | 4/2003 |
| JP | A-2003-252855 | 9/2003 |
| JP | A-2004-2252 | 1/2004 |
| JP | A-2004-177666 | 6/2004 |
| JP | A-2004-179393 | 6/2004 |
| JP | A-2004-205685 | 7/2004 |
| JP | A-2004-531749 | 10/2004 |
| JP | A-2004-310019 | 11/2004 |
| JP | A-2004-341479 | 12/2004 |
| JP | A-2004-354554 | 12/2004 |
| JP | A-2005-15532 | 1/2005 |
| JP | A-2005-18054 | 1/2005 |
| JP | A-2005-48152 | 2/2005 |
| JP | A-2005-84365 | 3/2005 |
| JP | A-2005-84621 | 3/2005 |
| JP | A-2005-120636 | 5/2005 |
| JP | A-2005-128509 | 5/2005 |
| JP | A-2005-250434 | 9/2005 |
| JP | A-2005-331951 | 12/2005 |
| JP | A-2005-352104 | 12/2005 |
| JP | A-2006-53543 | 2/2006 |
| JP | A-2006-106311 | 4/2006 |
| JP | A-2006-117763 | 5/2006 |
| JP | A-2006-126301 | 5/2006 |
| JP | A-2006-227391 | 8/2006 |
| JP | A-2006-259249 | 9/2006 |
| JP | A-2006-259482 | 9/2006 |
| JP | A-2006-285095 | 10/2006 |
| JP | A-2006-293207 | 10/2006 |
| JP | A-2006-293298 | 10/2006 |
| JP | A-2006-301145 | 11/2006 |
| JP | A-2007-17949 | 1/2007 |
| JP | A-2007-17950 | 1/2007 |
| JP | A-2007-65161 | 3/2007 |
| JP | A-2007-140461 | 6/2007 |
| JP | A-2007-145797 | 6/2007 |
| JP | A-2007-146149 | 6/2007 |
| JP | A-2007-163846 | 6/2007 |
| JP | A-2007-164148 | 6/2007 |
| JP | A-2002-214774 | 7/2007 |
| JP | A-2007-171895 | 7/2007 |
| JP | A-2007-199653 | 8/2007 |
| JP | A-2007-226170 | 9/2007 |
| JP | A-2007-226204 | 9/2007 |
| JP | A-2007-316188 | 12/2007 |
| JP | A-2007-316282 | 12/2007 |
| JP | A-2008-26600 | 2/2008 |
| JP | A-2008-39811 | 2/2008 |
| JP | A-2008-65303 | 3/2008 |
| JP | A-2008-81646 | 4/2008 |
| JP | A-2008-83668 | 4/2008 |
| JP | A-2008-96684 | 4/2008 |
| WO | WO 2004/074242 A2 | 9/2004 |
| WO | WO 2008/099869 * | 8/2008 |
| WO | WO 2009/037981 * | 3/2009 |

OTHER PUBLICATIONS

Schaedeli et al., "Evaluation of Materials for 193-nm Lithography," *Journal of Photopolymer Science and Technology*, vol. 9, No. 3, pp. 435-446, 1996.

Nagahara et al., "Elimination of Resist Poisoning in Via-First Dual Damascene Process," *Journal of Photopolymer Science and Technology*, vol. 16, No. 3, pp. 351-362, 2003.

* cited by examiner

RESIST LOWER-LAYER COMPOSITION CONTAINING THERMAL ACID GENERATOR, RESIST LOWER LAYER FILM-FORMED SUBSTRATE, AND PATTERNING PROCESS

BACKGROUND OF THE INVENTION

1. Field of the Invention

The present invention relates to a resist lower layer composition, a resist lower layer film-formed substrate and a patterning process used for formation of a layer lower than a resist upper layer film, which is useful for a multi-layer resist method favorably used in microfabrication in manufacturing of a semiconductor device and the like.

2. Description of be Related Art

As LSI is progressing toward a higher integration and a faster speed in recent years, further miniaturization of a pattern rule is required. Under such a movement, a lithography using a light exposure, which is a widely used technology today, is reaching a limit of its resolution power inherent to a wavelength of a light source.

As a light source for a lithography used in a resist patterning process, light-exposures with a g-line (436 nm) or an i-line (365 nm) of a mercury lamp have been widely used. For further miniaturization, a method in which an exposing light is shifting toward a shorter wavelength has been considered to be effective. Accordingly, in place of an i-line (365 nm), a KrF excimer laser (248 nm), which emits a shorter wavelength than the i-line, has been used in a mass production process for a 64 Mbit DRAM. However, for production of DRAM with an integration of 1 G or more, which requires a further miniaturized process technology (processing dimension of 0.13 µm or less), a light source with a further shorter wavelength is required, and thus, a lithography using an ArF excimer laser (193 nm) has been investigated particularly.

On the other hand, it has been known in the past that a multi-layer resist process such as a two-layer resist method is excellent in formation of a pattern having a high aspect ratio on a nonplanar substrate. As for a two-layer resist method, to develop a two-layer resist film by a generally used alkaline developer, a silicone polymer having a hydrophilic group such as a hydroxy group and a carboxyl group is preferable.

As such a silicone polymer, a silicone-type positive resist composition of chemically amplified type using a base resin, which is obtained by protecting a part of a phenolic hydroxy group of polyhydroxybenzyl silsesquioxane, a stable alkaline-soluble silicone polymer, with a t-Boc group, together with an acid generator is proposed for a KrF excimer laser (see, for examples, Japanese Patent Laid-Open (kokai) No. H6-118651 and SPIE Vol. 1925 (1993), p. 377). For an ArF eximer laser, a positive resist composition based on a silsesquioxane whose cyclohexyl carboxylic acid is substituted with an acid-labile group is proposed (see, for example Japanese Patent Laid-Open (kokai) No. H10-324748, Japanese Patent Laid-Open (kokai) No. H11-302382, and SPIE Vol. 3333 (1998), p. 62). Further, a positive resist composition based on a silsesquioxane having a hexafluoroisopropanol as a soluble group is proposed for an $F_2$ excimer laser (see, for example, Japanese Patent Laid-Open (kokai) No. 2002-55456). The above-mentioned polymers contain a polysilsesquioxane having a ladder skeleton in their main chain made by polycondensation of a trialkoxy silane or a trihalogenated silane.

As a silicone polymer having a silicon pendant on its side chain, a polymer of a silicon-containing (meth)acrylate ester is proposed (see, for example Japanese Patent Laid-Open (kokai) No. H9-110938 and J. Photopolymer Sci. and Technol., Vol. 9, No. 3 (1996), p. 435-446).

A resist lower layer film in a two-layer resist method is formed of a hydrocarbon compound, which can be etched by an oxygen gas, and in addition, which is desired to have a high etching resistance because it becomes a mask when a substrate under it is etched. For etching by an oxygen gas when etching of the resist lower layer film using a resist upper layer film as a mask, the resist lower layer film is desired to be composed of only a hydrocarbon, not containing a silicon atom. In addition, the resist lower layer film desires to have a function as an anti-reflection film in order to improve a controllability of a line width of a silicon-containing resist upper layer film and to form less bumps on a pattern sidewall and to reduce collapsing of a pattern by a standing wave. Specifically, a reflectance from a resist lower layer film to a resist upper layer film is desired to be made 1% or less.

Meanwhile, a three-layer resist method has been proposed which is configured to stack: a single-layer resist without containing silicon, as a resist upper layer film; a resist intermediate-layered film containing silicon, thereunder; and a resist lower layer film comprising an organic film, thereunder (see J. Vac. Sci. Technol., 16(6), November/December 1979, for example). Generally, single-layer resists are more excellent in resolution than silicon-containing resists, and it is possible to adopt a single-layer resist exhibiting a higher resolution as an exposure imaging layer in the three-layer resist method. As the resist intermediate-layered film, a spin-on-glass (SOG) film is used, and many SOG films have been proposed.

Here, the optimum optical constants of a resist lower layer film for restricting a substrate reflection in the three-layer resist method are different from those in the two-layer resist method.

Although the two-layer resist method and the three-layer resist method are the same in terms of the purpose to restrict the substrate reflection as less as possible, concretely, down to 1% or less, the three-layer resist method is allowed to cause one or both of a resist intermediate-layered film and a resist lower layer film to possess an antireflective effect whereas the two-layer resist method is configured to cause only a resist lower layer film to possess an antireflective effect.

Incidentally, silicon-containing layer compositions configured to possess antireflective effects have been proposed in U.S. Pat. No. 6,506,497 and U.S. Pat. No. 6,420,088 and the like, for example.

Further, it is also known that a multi-layered antireflective film has a higher antireflective effect than a single-layered antireflective film, and multi-layered antireflective films are being widely and industrially used as antireflective films of optical parts, eyeglasses, and the like. Namely, it is possible to obtain a higher antireflective effect by causing both a silicon-containing resist intermediate-layered film and a resist lower layer film to possess antireflective effects.

Moreover, the resist lower layer film in case of the three-layer resist method is required to possess a higher etching resistance during substrate processing, in addition to the effect as an antireflective film.

Thus, as a resist lower layer film for the three-layer resist method, it is preferable to use a polymer having a higher etching resistance, containing more aromatic groups, and having a higher ratio of carbon atoms.

Under such circumstances, low-dielectric insulator films have been recently and increasingly used as layers to be processed of substrates. As low-dielectric insulator films for achieving specific dielectric constants of 2.5 or less, porous silicas having specific dielectric constants of 1 and having vacancies have been investigated.

However, one of problems in the case of adopting low-dielectric insulator films based on porous silica, is footing (poisoning) of a positive resist after development. As a reason thereof, it has been considered that amine substances are adsorbed to vacancy portions, and the amine substances are released from the vacancy portions and passed through a resist lower layer film to cause a neutralizing reaction with acid in an overlying resist film to cause the footing, during a resist patterning process, particularly during baking (see J. Photopolymer Sci. and Technol. Vol. 16 No. 3 (2003) p351-361). It is therefore desired to elaborate a resist lower layer film capable of mitigating adverse effects such as footing in an overlying resist film to be caused by amine substances.

As methods for prevention of poisoning, there have been proposed a lower layer film configured to generate a sulfonic acid residue such as by heating (Japanese Patent Laid-Open (kokai) No. 2004-177666, and Japanese Patent Laid-Open (kokai) No. 2004-179393, for example), and a lower layer film additively including an amine salt of a polymeric fluorosulfonic acid (Japanese patent application No. 2005-120636, for example). Although lower layer films each additively including a polymer having an acidic group are free of concern of evaporation of the acid due to baking, the acidic group is fixed, thereby exhibiting such a disadvantage of a decreased ability to neutralize a basic substance which is produced from a substrate as a cause of poisoning.

Methods have been conventionally known to improve resist pattern profile in a manner to add an acid or an acid generator into a layer lower than a resist upper layer film, and there have been exemplarily proposed: an intermediate-layered film adapted to a three-layer resist method and comprising a silicone resin additively including an ammonium salt for generating an antimonate (Japanese Patent Laid-Open (kokai) No. H5-267158, for example); an intermediate-layered film for a three-layer resist method and additively including an acid generator (Japanese Patent Laid-Open (kokai) No. H5-291130, for example); and the like.

However, although the added type of acid generator exhibits a higher anti-poisoning ability when the produced acid remains in the film, the acid generator brings about a problem of a lowered anti-poisoning ability due to evaporation of the acid by baking upon cross-linking. In this respect, although a higher anti-poisoning effect can be expected by perfluorosulfonic acid as a super strong acid, this acid has a lower boiling point and thus evaporates upon baking, thereby deteriorating the anti-poisoning effect.

Although alkyl sulfonic acids such as camphorsulfonic acid are high in boiling point, they are weak acids and are thus lower in amine trapping ability. Further, although inorganic acids such as antimonate are strong acids and are high in boiling point, metallic acids are not allowed to be used in a semiconductor application. In turn, an ammonium salt has a thermal decomposition temperature lower than those of onium salts such as iodonium salt and sulfonium salt, and is capable of generating an acid by low-temperature baking to thereby cure an associated film. The lowered baking temperature means that evaporation of an acid is prevented to improve an anti-poisoning effect. Here, there have been disclosed: a lower layer film including an acid generator of an ammonium salt type of toluenesulfonic acid (Japanese Patent Laid-Open (kokai) No. 2003-114533 and Japanese Patent Laid-Open (kokai) No. 2005-331951, for example); exemplification of nonafluorobutanesulfonate triethylamine salt in the body text (Japanese patent application No. 2002-372829, for example); and example of nonafluorobutanesulfonate tripropylamine salt (Japanese patent application No. 2004-28506, for example).

In such multi-layer resist methods, acid crosslinking agents, thermal acid generators and the like in resist lower-layer compositions have increasingly come to exhibit important roles. For promotion of a cross-linking reaction by heating, there is required a thermal acid generator for generating a strong acid. Although thermal acid generators for generating perfluoroalkylsulfonic acids have been preferably adopted for that purpose, trifluoromethanesulfonic acid, nonafluorobutanesulfonic acid, and the like having lower molecular weights are problematically high in volatility, thereby bringing about a possibility of volatilization upon cross-linking reaction. Meanwhile, although perfluorooctanesulfonic acid having a long-chain alkyl group is not so problematic in terms of volatility, its biologically concentrating property and accumulative property caused by a stability (indecomposability), hydrophobicity, and lipophilicity derived from C—F bonds have become problematic, thereby internally containing a harmfulness problem and an environmental problem. The Environmental Protection Agency (EPA) in US has covered 13 substances and 75 substances relating to perfluorooctanesulfonic acids: PFOS's in the significant new use rules, respectively. Note that although adoptions of the 75 substances for resist application are exempted from notification, it is desired to elaborate a composition so as to exclude usage of PFOS's in view of the aforementioned harmfulness problem and environmental problem.

To cope with the problem concerning PFOS's, elaborations have been conducted by companies to obtain partially fluorine-substituted alkyl sulfonic acids configured to have decreased fluorine substitution rates, respectively. For example, Japanese translation of PCT international application No. 2004-531749 has elaborated α,α-difluoroalkyl sulfonate from α,α-difluoroalkene and a sulfur compound, and exemplified a resist composition containing a photoacid generator for generating a corresponding sulfonic acid by exposure, concretely, containing (4-tert-butylphenyl)iodonium-1, 1-difluoro-1-sulfonate-2-(1-naphthyl)ethylene; and the Japanese Patent Laid-Open (kokai) No. 2004-2252 has elaborated α,α,β,β-tetrafluoroalkyl sulfonate from α,α,β,β-tetrafluoro-α-iodoalkane and a sulfur compound, and exemplified a photoacid generator for generating a corresponding sulfonic acid, and a resist composition. Further, although synthesis examples of actual compounds are not disclosed in the Japanese Patent Laid-Open (kokai) No. 2002-214774, numerous photoacid generators for generating partially fluorinated alkyl sulfonic acids and resist compositions are disclosed therein. However, numerous problems are left, such as difficulties in obtainment of intermediate products of raw materials and in production methods. Moreover, descriptions in the references are related to utilization of such sulfonates as photoacid generators only, and no descriptions are found therein concerning utilization of the sulfonates in resist lower-layer compositions.

In this way, it is desired to elaborate a resist lower-layer composition which exhibits a higher anti-poisoning effect in a multi-layer resist method, and which is low in environment load.

SUMMARY OF THE INVENTION

The present invention has been attained in view of the above circumstances, and it is therefore an object of the present invention to provide a resist lower-layer composition in a multi-layer resist method (particularly, a two-layer resist method and a three-layer resist method), which composition is used to form a layer lower than a photoresist layer acting as a resist upper layer film, which composition becomes insoluble or poorly-soluble in an alkaline developer after formation of the lower layer, and which composition is capable of forming a resist lower layer film, intermediate-layered film, and the like having a higher anti-poisoning effect and exhibiting a lower load to the environment.

To solve the above problem, the present invention provides a resist lower-layer composition configured to be used by a multi-layer resist method used in lithography to form a layer lower than a photoresist layer acting as a resist upper layer film, wherein the resist lower-layer composition becomes insoluble or poorly-soluble in an alkaline developer after formation of the lower layer, and wherein the resist lower-layer composition comprises, at least, a thermal acid generator for generating an acid represented by the general formula (1) by heating at a temperature of 100° C. or higher:

$$RCOO-CH_2CF_2SO_3^-H^+ \quad (1)$$

wherein, R represents a substituted or unsubstituted linear, branched, or cyclic alkyl group having 1 to 20 carbon atoms, or a substituted or unsubstituted aryl group having 6 to 14 carbon atoms.

In this way, by using the resist lower-layer composition comprising, at least, the thermal acid generator which generates an acid represented by the general formula (1) by heating at a temperature of 100° C. or higher so as to form a layer lower than a photoresist layer in a multi-layer resist method, the acid represented by the general formula (1) is low in volatility and thus a large amount of the acid is left within the applicable film even after baking to thereby enable neutralization of amine contaminants brought about from a substrate, so that adverse effects such as footing (poisoning) of the overlying resist film can be reduced to enable formation of a pattern with extremely higher precision. Further, the thermal acid generator which generates the acid represented by the general formula (1) exhibits a higher alkaline hydrolysis property, thereby enabling a lower load to the environment.

Preferably, the resist lower-layer composition further comprises a base resin and an acid crosslinking agent.

In this way, the resist lower-layer composition is allowed to include the base resin and the acid crosslinking agent. Particularly, the acid represented by the general formula (1) is a super strong acid, thereby enabling to form a sufficient film by a cross-linking reaction between the acid crosslinking agent and the base resin.

Preferably, the thermal acid generator for generating the acid represented by the general formula (1) is an onium salt represented by the general formula (2):

$$RCOO-CH_2CF_2SO_3^-(R^1)_mA^+ \quad (2)$$

wherein, R represents the same meaning as before;
A represents a nitrogen atom, sulfur atom, or iodine atom;
m is 4 when A is a nitrogen atom, 3 when A is a sulfur atom, and 2 when A is an iodine atom; and
$R^1$'s mutually independently represent a hydrogen atom, a substituted or unsubstituted linear, branched, or cyclic alkyl group, alkenyl group, or oxoalkyl group having 1 to 10 carbon atoms, or a substituted or unsubstituted aryl group, aralkyl group, or aryloxoalkyl group having 6 to 18 carbon atoms, or alternatively, two or more of $R^1$'s may be mutually bonded to form a ring together with A in the formula, provided that $R^1$ does not represent a hydrogen atom when A is a sulfur atom or iodine atom.

Further, it is preferable that the thermal acid generator for generating the acid represented by the general formula (1) is a thermal acid generator represented by the general formula (3):

$$RCOO-CH_2CF_2SO_3^-(R^1)_4N^+ \quad (3)$$

wherein, R represents the same meaning as before; and
$R^1$'s mutually independently represent a hydrogen atom, a substituted or unsubstituted linear, branched, or cyclic alkyl group, alkenyl group, or oxoalkyl group having 1 to 10 carbon atoms, or a substituted or unsubstituted aryl group, aralkyl group, or aryloxoalkyl group having 6 to 18 carbon atoms, or alternatively, two or more of $R^1$'s may be mutually bonded to form a ring together with N in the formula.

In this way, examples of the thermal acid generator which generates the acid represented by the general formula (1) include those represented by the general formula (2), and those represented by the general formula (3). Particularly, ammonium salts represented by the general formula (3) are readily available and thus advantageous from an aspect of cost, and thermal acid generation temperatures thereof are easy to control.

Preferably, the base resin of the resist lower-layer composition has an acid-crosslinking property. In this way, the base resin having an acid-crosslinking property is usable.

Preferably, the base resin of the resist lower-layer composition contains a silicon atom. It is preferable that the base resin of the resist lower-layer composition contains none of a silicon atom, titanium atom, and germanium atom, but containing carbons in an amount of 50 mass % or more.

In this way, as the base resin of the resist lower-layer composition, it is possible to use: one containing a silicon atom; or one containing none of a silicon atom, titanium atom, and germanium atom, but containing carbons in an amount of 50 mass % or more.

Preferably, the resist lower-layer composition further comprises an organic solvent.

In this way, as the resist lower-layer composition, it is possible to use one including the organic solvent.

The present invention further provides a substrate including a layer to be processed, wherein the substrate comprises, at least, a resist lower layer film formed by using the above-described resist lower-layer composition, on the layer to be processed.

In this way, by using the substrate formed with the resist lower layer film on the layer to be processed by adopting the above-described resist lower-layer composition to form a pattern on the substrate by lithography, it is possible to make the pattern formed on the substrate to be fine with higher precision.

Preferably, the layer to be processed of the substrate is a low-dielectric film having a specific dielectric constant of 3.5 or less or a nitride film.

When the layer to be processed of the substrate is a low-dielectric film having a specific dielectric constant of 3.5 or less or a nitride film, it is possible to prevent electric leakage among wirings.

The present invention further provides a patterning process for forming a pattern on a substrate by lithography, comprising the steps of: at least, forming a resist lower layer film on a layer to be processed of the substrate, by using the above-described resist lower-layer composition;

forming a resist upper layer film on the resist lower layer film by using a photoresist composition, to form at least two multi-layer resist films;

subsequently conducting exposure of a pattern circuit region of the resist upper layer film, developing it by a developer to form a resist pattern in the resist upper layer film, and etching the resist lower layer film by using the thus obtained resist pattern as a mask to form a resist lower layer film pattern; and etching the layer to be processed of the substrate by using the thus obtained resist lower layer film pattern as a mask, to form a pattern on the substrate.

By using such a two-layer resist method; it is possible to form a fine pattern on a substrate with higher precision.

Preferably, the resist lower layer film is formed by using a resist lower-layer composition including a base resin containing a silicon atom; and wherein the resist upper layer film is formed by using a photoresist composition containing no silicon atoms. Further, it is preferable that the resist lower layer film is formed by using a resist lower-layer composition including a base resin containing none of a silicon atom, titanium atom, and germanium atom, but containing carbons in an amount of 50 mass % or more; and wherein the resist upper layer film is formed by using a photoresist composition containing a silicon atom.

In this way, it is possible to increase an etching selectivity ratio, by causing one of the resist lower layer film composition and the resist upper layer film composition to contain a silicon atom.

The present invention further provides a patterning process for forming a pattern on a substrate by lithography, comprising the steps of: at least, forming a resist lower layer film on a layer to be processed of the substrate, by using the above-described resist lower-layer composition;

forming an intermediate layer containing a silicon atom on the resist lower layer film;

forming a resist upper layer film on the intermediate layer by using a photoresist composition containing no silicon atoms, to form at least three multi-layer resist films;

subsequently conducting exposure of a pattern circuit region of the resist upper layer film, developing it by a developer to form a resist pattern in the resist upper layer film, and dry etching the intermediate layer by using the thus obtained resist pattern as a mask to form an intermediate layer pattern;

etching the resist lower layer film by using the intermediate layer pattern as a mask, to form a resist lower layer film pattern; and etching the layer to be processed of the substrate by using the thus obtained resist lower layer film pattern as a mask, to form a pattern on the substrate.

In this way, the resist lower layer film formed by using the resist lower-layer composition of the present invention exhibits an excellent antireflective effect in combination with the resist intermediate layer, and the resist upper layer film containing no silicon atoms has an advantage of excellent resolution as compared with those containing silicon atoms. Thus, the pattern to be transferred to the intermediate layer, as well as the pattern to be transferred to the lower layer film can be made to be highly precise. Accordingly, by etching the layer to be processed of the substrate by using the resist lower layer film having the thus transferred pattern as a mask to form a pattern on the substrate, it is possible to make the pattern formed on the substrate to be more highly precise.

It is preferable that a low-dielectric film having a specific dielectric constant of 3.5 or less or a nitride film is used as the layer to be processed of the substrate.

When the layer to be processed of the substrate is a low-dielectric film having a specific dielectric constant of 3.5 or less or a nitride film, it is possible to prevent electric leakage among wirings.

As described above, in the case of the resist lower-layer composition of the present invention additively including the thermal acid generator which generates the acid represented by the general formula (1), the acid does not volatilize even during baking, thereby enabling to neutralize amine contaminants brought about from the substrate during the resist patterning process. Thus, adverse effects such as footing of the overlying resist film can be reduced to enable formation of a pattern with extremely higher precision. Further, the thermal acid generator for generating the sulfonic acid has an acid strength sufficient for cross-linking the acid crosslinking agent with the resin and is also low in volatility, so that the thermal acid generator is capable of cross-linking the acid crosslinking agent with the resin by heating, thereby achieving a sufficient film formation. Further, the ester site is alkaline hydrolyzed upon treatment of waste resist liquid after fabrication of devices, so that the thermal acid generator can be converted into compounds having lower molecular weights and lower accumulative properties, thereby enabling prevention of a load to the environment after completion of its usage in lithography.

DETAILED DESCRIPTION OF THE PREFERRED EMBODIMENTS

Figure 1:
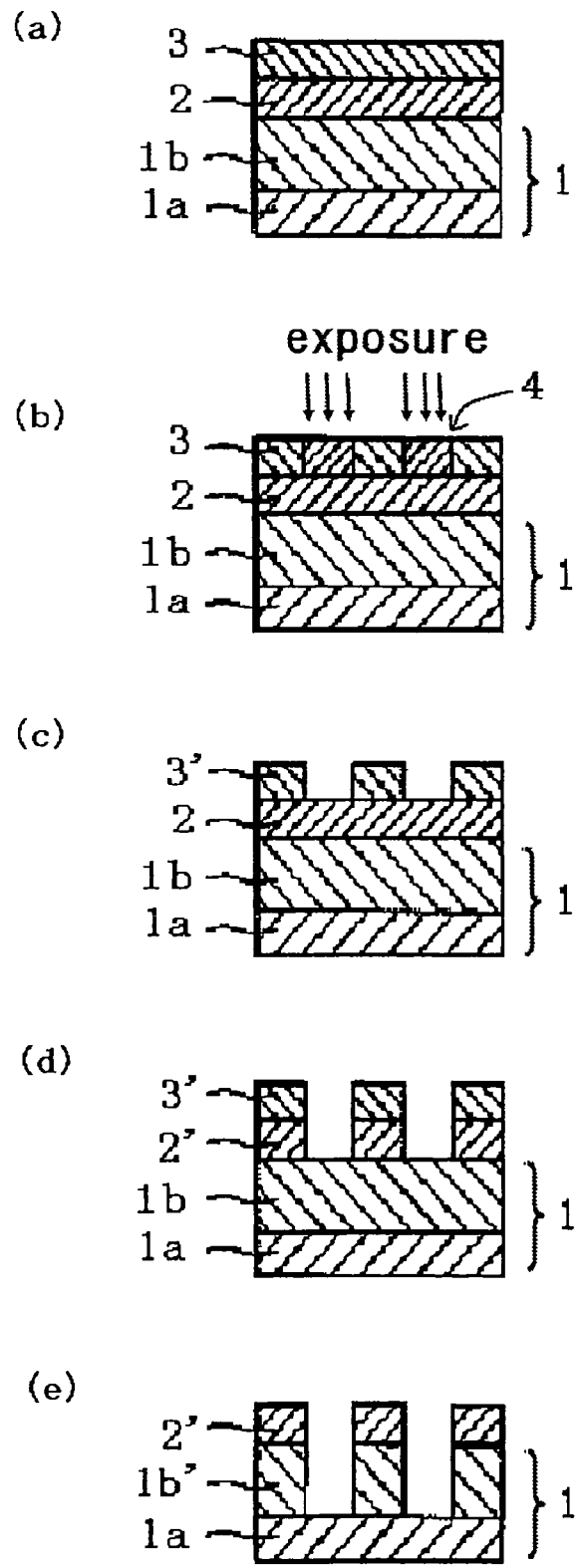
FIG. 1 is an explanatory view of an example of a patterning process of the present invention based on a two-layer resist method.

The present invention will be explained more specifically.

As described above, when a low-dielectric insulator film based on porous silica is adopted as a layer to be processed of a substrate, amine substances are adsorbed to vacancy portions, and the amine substances are released from the vacancy portions and passed through a resist lower layer film to cause a neutralizing reaction with acid in an overlying resist film to cause footing or the like, during a resist patterning process, particularly during baking. This has caused a problem of difficulty in forming a resist pattern with higher precision in a resist upper layer film.

To such a problem, various investigations have been conventionally conducted for acid generators. However, this has rather caused such problems of: a deteriorated anti-poisoning ability due to occurrence of evaporation of acid during baking upon cross-linking of a base resin; a lower ability of amine trapping due to weakness of acid; a load to the environment; and difficulties in production methods.

To solve the above problems, the present inventors have earnestly conducted repetitive investigations, and have conceived that amine contaminants from a substrate can be neutralized in a layer lower than a resist upper layer film when a thermal acid generator having a higher boiling point and adapted to generate super strong acid is added into a resist lower-layer composition, thereby narrowly achieving the present invention.

The present inventors have found out that, in the case of adopting the resist lower-layer composition comprising, at least, the thermal acid generator for generating the acid represented by the general formula (1) by heating at a temperature of 100° C. or higher, the acid represented by the general formula (1) has a higher boiling point and is a super strong acid, so that a large amount of the acid is left within the applicable film even after baking to thereby enable neutralization of amine contaminants brought about from a substrate. Further, the present inventors have found out that the thermal acid generator for generating the sulfonic acid has an acid strength sufficient for cross-linking the acid crosslinking agent with the resin, thereby achieving a sufficient film formation by heating. Moreover, the present inventors have found out that the thermal acid generator included in the resist lower-layer composition of the present invention has an ester site, so that the acid generator is alkaline hydrolyzed upon treatment of waste resist liquid after fabrication of devices, thereby lowering a load to the environment.

Namely, to solve the above problems, the present invention provides a resist lower-layer composition configured to be used by a multi-layer resist method used in lithography to form a layer lower than a photoresist layer acting as a resist upper layer film, wherein the resist lower-layer composition becomes insoluble or poorly-soluble in an alkaline developer after formation of the lower layer, and wherein the resist lower-layer composition comprises, at least, a thermal acid generator for generating an acid represented by the general formula (1) by heating at a temperature of 100° C. or higher:

$$RCOO-CH_2CF_2SO_3^--H^+ \quad (1)$$

wherein, R represents a substituted or unsubstituted linear, branched, or cyclic alkyl group having 1 to 20 carbon atoms, or a substituted or unsubstituted aryl group having 6 to 14 carbon atoms.

As described above, the resist lower-layer composition of the present invention is a novel composition additively including the thermal acid generator for generating 2-(alkylcarbonyloxy)-1,1-difluoroethanesulfonic acid, or 2-(arylcarbonyloxy)-1,1-difluoroethanesulfonic acid represented by the general formula (1), by heating at a temperature of 100° C. or higher.

Further, the thermal acid generator for generating the acid represented by the general formula (1) is extremely low in volatilization amount, even upon cross-linking of the base resin in the resist lower-layer composition by baking. As such, even when amine substances are released from a substrate during resist patterning process, the amine substances can be neutralized in the resist lower layer film by virtue of the acid generated by the acid generator. Thus, adopting the resist lower-layer composition of the present invention enables mitigation of adverse effects such as footing in an overlying resist film, thereby forming a pattern with extremely higher precision. Further, the thermal acid generator for generating the sulfonic acid has an acid strength sufficient for cross-linking the acid crosslinking agent with the resin, so that the thermal acid generator is capable of cross-linking the acid crosslinking agent with the resin by heating, thereby achieving a sufficient film formation.

Here, R represents a substituted or unsubstituted linear, branched, or cyclic alkyl group having 1 to 20 carbon atoms, or a substituted or unsubstituted aryl group having 6 to 14 carbon atoms. The substituent are exemplified alkyl group, aryl group, —O—, —O—C(=O)—, —C(=O)—, —C(=O)—O—, hydroxyl group, and the like. The substituent may include a double bond and hydrogen atom thereof may be substituted with fluorine atoms wherein provided that not all hydrogen atoms are substituted with fluorine atoms.

Here, more concrete examples of R include methyl group, ethyl group, n-propyl group, sec-propyl group, cyclopropyl group, n-butyl group, sec-butyl group, iso-butyl group, tert-butyl group, n-pentyl group, cyclopentyl group, n-hexyl group, cyclohexyl group, n-octyl group, n-decyl group, n-dodecyl group, 1-adamantyl group, 2-adamantyl group, bicycle[2.2.1]hepten-2-yl group, phenyl group, 4-methoxyphenyl group, 4-tert-butylphenyl group, 4-biphenyl group, 1-naphthyl group, 2-naphthyl group, 10-anthranyl group, 2-furanyl group, 4-oxo-adamantane-1-yl group, 4-oxo-cyclohexyl group and following groups. (Note that, a broken line in the formula represents a bond hands.)

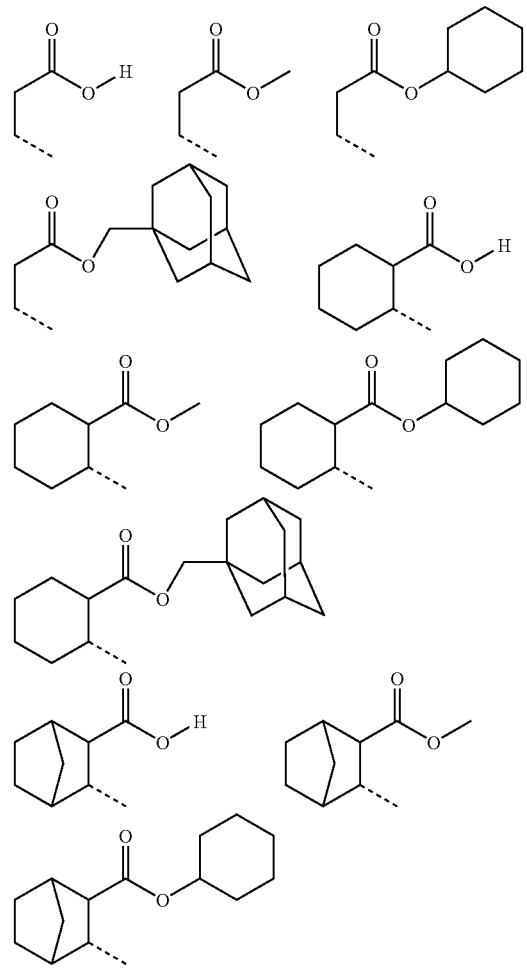

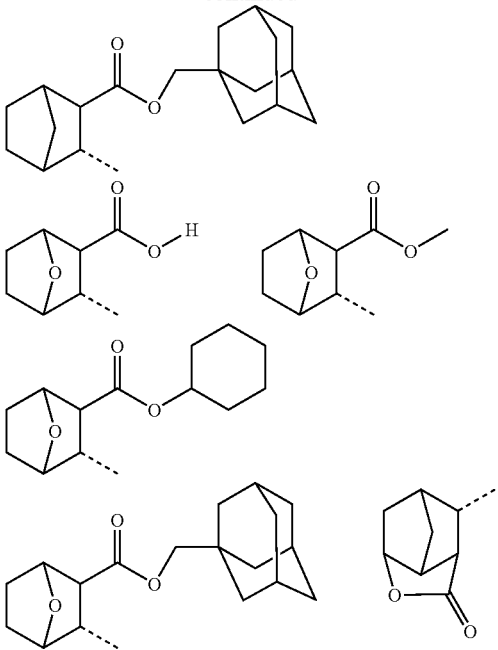

Preferred among R groups are tert-butyl group, cyclohexyl group, 1-adamantyl group, phenyl group, tert-butylphenyl group, 4-methoxyphenyl group, 4-biphenyl group, 1-naphthyl group, 2-naphthyl group and the like. More preferred are tert-butyl group, cyclohexyl group, phenyl group, 4-tert-butylphenyl group and the like.

As the thermal acid generator included in the resist lower-layer composition of the present invention, the compound represented by an onium salt, oxime, and imide each having 1,1-difluoro-2-acyloxyethane-1-sulfonate, which may include carbonyl group, carboxyl group, carboxylic acid ester or lactone structure, can be used. More concrete examples of the thermal acid generator include following N-sulfonyloxyimide compound, following oxime sulfonate compound and onium salt (iodonium salt, sulfonium salt and ammonium salt) to be described below and the like. The thermal acid generator is not particularly limited thereto as far as it generates the acid represented by the general formula (1). Note that, since known photoacid generators are configured to generate acids not only by irradiation of high-energy beams but also by heating, the compound which includes sulfonic acid represented by the general formula (1) in sulfonic acid site of the known photo acid generator can be used as the thermal acid generator of the present invention.

A N-sulfonyloxyimide compound represented by the following general formula (4) may also be used for the thermal acid generators of the present invention.

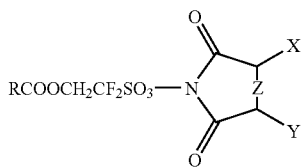

(4)

wherein R represents the same meanings as before. X and Y are each independently hydrogen or a substituted or unsubstituted alkyl group having 1 to 6 carbon atoms, or X and Y may bond together to form a saturated or unsaturated ring having 6 to 12 carbon atoms with the carbon atoms to which they are attached, and Z is a single bond, double bond, methylene group or oxygen atom.

Further, a naphthalene-1,8-diyl group may be represented by combination X, Y, Z and a carbon atom bonded to carbonyl together. Illustrative examples of the imide skeleton excluding the sulfonate moiety are given below. For the imide skeleton, reference may be made to Japanese Patent Laid-Open (kokai) No. 2003-252855. (Note that, a broken line in the formula represents a bonding portion with the sulfonate moiety)

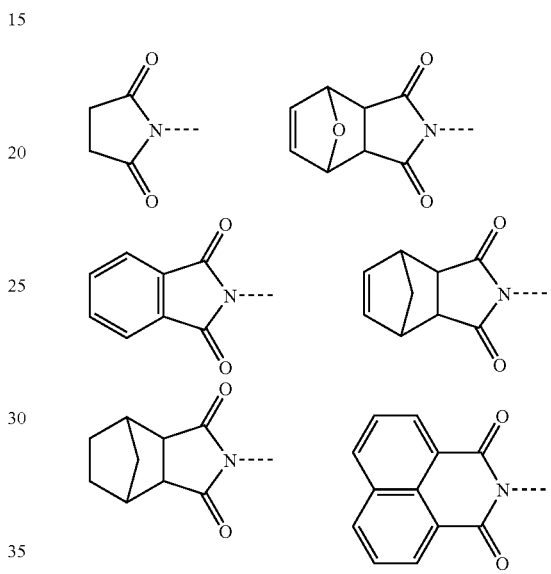

An oxime sulfonate compound represented by the following general formula (5) may also be used for the thermal acid generators of the present invention.

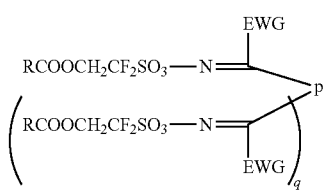

(5)

wherein R represents the same meanings as before. q is 0 or 1; when q is 1, p is a substituted or unsubstituted alkyl group having 1 to 20 carbon atoms or a substituted or unsubstituted aryl group having 6 to 20 carbon atoms; when q is 1, p is a substituted or unsubstituted alkylene group having 1 to 20 carbon atoms or a substituted or unsubstituted arylene group having 6 to 20 carbon atoms; and EWG is a cyano, trifluoromethyl, perfluoroethyl, perfluoropropyl, 5H-perfluoropentyl, 6H-perfluorohexyl, nitro or methyl group, and when q is 1, two EWG's may bond together to form a ring of 6 carbon atoms with the carbon atoms to which they are attached. The skeletons of these oxime sulfonates are described in U.S. Pat. No. 6,261,738, Japanese Patent Laid-Open (kokai) No. H9-95479, Japanese Patent Laid-Open (kokai) No. H9-208554, Japanese Patent Laid-Open (kokai) No H9-230588, Japanese Patent No. 2906999, Japanese Patent Laid-Open (kokai) No. H9-301948, Japanese Patent Laid-Open (kokai) No. 2000-314956, Japanese Patent Laid-Open (kokai) No. 2001-233842, and WO2004/074242.

Exemplary skeletons of oxime sulfonates excluding the sulfonate moiety are given below. Note that, a broken line represents a bonding portion with the sulfonate moiety.

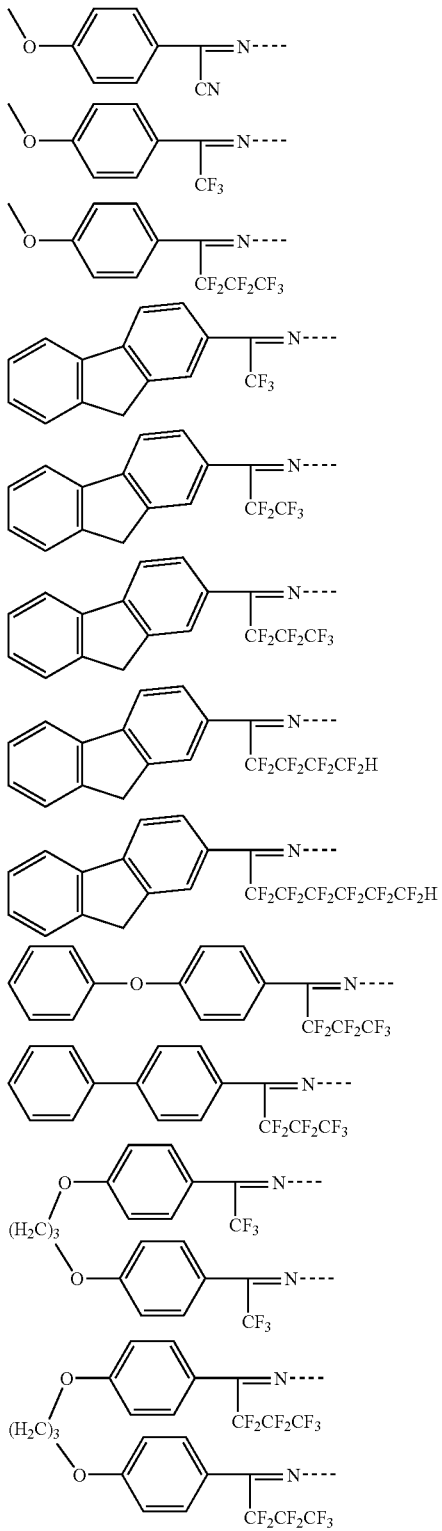

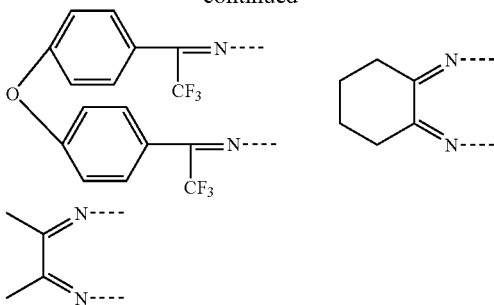

Further, as the thermal acid generator in the present invention, an onium salt represented by the general formula (2) may be used:

$$RCOO-CH_2CF_2SO_3^-(R^1)_mA^+ \quad (2)$$

wherein, R represents the same meaning as before;

A represents a nitrogen atom, sulfur atom, or iodine atom;

m is 4 when A is a nitrogen atom, 3 when A is a sulfur atom, and 2 when A is an iodine atom; and $R^1$'s mutually independently represent a hydrogen atom, a substituted or unsubstituted linear, branched, or cyclic alkyl group, alkenyl group, or oxoalkyl group having 1 to 10 carbon atoms, or a substituted or unsubstituted aryl group, aralkyl group, or aryloxoalkyl group having 6 to 18 carbon atoms, or alternatively, two or more of $R^1$'s may be mutually bonded to form a ring together with A in the formula, provided that $R^1$ does not represent a hydrogen atom when A is a sulfur atom or iodine atom.

Examples of the substituent group in $R^1$ include hydroxyl group, alkoxy group, halogen and carbonyl group. Concrete examples of alkyl group include methyl group, ethyl group, propyl group, iso-propyl group, n-butyl group, sec-butyl group, tert-butyl group, pentyl group, hexyl group, heptyl group, octyl group, cyclopentyl group, cyclohexyl group, cycloheptyl group, cyclopropylmethyl group, 4-methylcyclohexyl group, cyclohexylmethyl group, norbornyl group, and adamantyl group. Examples of alkenyl groups include vinyl group, allyl group, propenyl group, butenyl group, hexenyl group, and cyclohexenyl groups. Examples of oxoalkyl groups include 2-oxocyclopentyl group, 2-oxocyclohexyl group, 2-oxopropyl group, 2-oxoethyl group, 2-cyclopentyl-2-oxoethyl, 2-cyclohexyl-2-oxoethyl, and 2-(4-methylcyclohexyl)-2-oxoethyl groups. Examples of aryl groups include phenyl group, naphthyl group, and thienyl group; alkoxyphenyl groups such as 4-hydroxy phenyl group, p-methoxyphenyl group, m-methoxyphenyl group, o-methoxyphenyl group, p-ethoxyphenyl group, p-tert-butoxyphenyl group, and m-tert-butoxyphenyl group; alkylphenyl groups such as 2-methylphenyl group, 3-methylphenyl group, 4-methylphenyl group, ethylphenyl group, 4-tert-butylphenyl group, 4-butylphenyl group, and 2,4-dimethylphenyl group; alkylnaphthyl groups such as methylnaphthyl group and ethylnaphthyl group; alkoxynaphthyl groups such as methoxynaphthyl group and ethoxynaphthyl group; dialkylnaphthyl groups such as dimethylnaphthyl group and diethylnaphthyl group; and dialkoxynaphthyl groups such as dimethoxynaphthyl group and diethoxynaphthyl group. Examples of aralkyl groups include benzyl group, 1-phenylethyl group, and 2-phenylethyl group. Examples of aryloxoalkyl groups include 2-aryl-2-oxoethyl groups such as 2=phenyl-2-oxoethyl group, 2-(1-naphthyl)-2-oxoethyl group, and 2-(2-naphthyl)-2-oxoethyl group.

Further, in the case where two or more of $R^1$'s are mutually bonded to form a ring structure together with a nitrogen atom, structures such as piperidine, morpholine, pyridine, quinoline, acridine, imidazole, benzimidazole and the like are exemplified, and the nitrogen atom may be protonated and alkylated. As a substituent group, aryl group having cross-linkable substituent group such as an acryloyloxy group, methacryloyloxy group and the like, concrete example include 4-(acryloyloxy)phenyl group, 4-(methacryloyloxy) phenyl group, 4-vinyloxyphenyl group, 4-vinylphenyl group and the like. Further, in the case where two or more of $R^1$'s are mutually bonded to form a ring structure together with a sulfur atom, structures such as tetrahydrothiophene, 1,4-thioxane, dibenzothiophene, phenoxathiine and the like are exemplified.

The other $R^1$ is the same as one represented by above mentioned formula (2).

As concrete examples of $(R^1)_mA^+$ include: in the case where A is a nitrogen atom, ammonium, trimethylammonium, tetramethylammonium, triethylammonium, tributylammonium, tetrabutylammonium, trioctylammonium, anilinium, 2,6-dimethylanilinium, N,N-dimethylanilinium, benzyltrimethylammonium, benzyltriethylammonium, benzyltripropylammonium, N-benzyl-N,N-dimethylanilinium, and N-(p-methoxy)benzyl-N,N-dimethylanilinium; in the case where A is a sulfur atom, triphenyl sulfonium, 4-hydroxyphenyldiphenylsulfonium, bis(4-hydroxyphenyl)phenylsulfonium, tris(4-hydroxyphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-ditert-butoxy phenyl)diphenylsulfonium, bis(3,4-ditert-butoxyphenyl)phenylsulfonium, tris(3,4-ditert-butoxyphenyl)sulfonium, diphenyl(4-thiophenoxy phenyl) sulfonium, (4-tert-butoxycarbonylmethyloxyphenyl) diphenylsulfonium, tris(4-tert-butoxycarbonylmethyloxyphenyl)sulfonium, (4-tert-butoxyphenyl)bis(4-dimethylaminophenyl)sulfonium, tris (4-dimethylaminophenyl)sulfonium, 2-naphthyldiphenylsulfonium, dimethyl-2-naphthylsulfonium, 4-hydroxy phenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl 2-thienyl sulfonium, 4-n-butoxynaphthyl-1-thiacyclopentanium, 2-n-butoxynaphthyl-1-thiacyclopentanium, 4-methoxynaphthyl-1-thiacyclopentanium, 2-methoxynaphthyl-1-thiacyclopentanium, 4-methylphenyldiphenylsulfonium, 4-ethylphenyldiphenylsulfonium, 4-tert-butylphenyldiphenyl sulfonium, 4-cyclohexylphenyldiphenyl sulfonium, 4-n-hexylphenyldiphenyl sulfonium, 4-n-octylphenyldiphenyl sulfonium, 4-methoxyphenyldiphenyl sulfonium, 4-ethoxyphenyldiphenyl sulfonium, 4-cyclohexyloxyphenyldiphenyl sulfonium, 4-n-hexyloxyphenyldiphenyl sulfonium, 4-n-octyloxyphenyldiphenyl sulfonium, 4-dodecyloxyphenyldiphenyl sulfonium, 4-trifluoromethylphenyldiphenyl sulfonium, 4-trifluoromethyloxyphenyldiphenyl sulfonium, 4-tert-butoxycarbonylmethyloxyphenyldiphenyl sulfonium, 10-phenylphenoxyathiinium, Preferably, triphenyl sulfonium, 4-tert-butylphenyldiphenyl sulfonium, 4-tert-butoxyphenyldiphenylsulfonium, tris(4-tert-butylphenyl)sulfonium, (4-tert-butoxycarbonylmethyloxyphenyl)diphenylsulfonium, diphenylmethylsulfonium, dimethylphenylsulfonium, 2-oxo-2-phenylethylthiacyclopentanium, 10-phenylphenoxyathiinium; in the case where A is a iodine atom, bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, 4-methacryloyloxy phenylphenyliodonium, preferably, (4-tert-butylphenyl) iodonium.

Which one among the above ammonium salts, sulfonium salts and iodonium salts is used is arbitrary. Note that, since a resist lower-layer composition is stored in the state of solution in many cases, unfavorable cross-linking reaction among acid crosslinking agents and resins are derived in the case that an acid are generated in the solution. As a result, problems such as gel-generating, variance of coated film thickness and deterioration of coating uniformity are derived in the following steps. Therefore, a thermal acid generator which generates an acid only upon heating is desired. For this stability, its thermal decomposition starting temperature, i.e., thermal acid generating temperature, is 100° C. or higher, preferably 150° C. or higher. Considering this thermal acid generating temperature, solubility in the solvent, residual after decomposition and the like, which one among the above ammonium salts, sulfonium salts and iodonium salts is used can be selected. Among these, ammonium salts are readily available and advantageous from an aspect of cost.

Further, as the thermal acid generator included in the resist lower layer composition of the present invention, an ammonium salt represented by the general formula (3) may be used:

$$RCOO-CH_2CF_2SO_3^-(R^1)_4N^+ \qquad (3)$$

wherein, R represents the same meaning as before; and $R^1$'s mutually independently represent a hydrogen atom, a substituted or unsubstituted linear, branched, or cyclic alkyl group, alkenyl group, or oxoalkyl group having 1 to 10 carbon atoms, or a substituted or unsubstituted aryl group, aralkyl group, or aryloxoalkyl group having 6 to 18 carbon atoms, or alternatively, two or more of $R^1$'s may be mutually, bonded to form a ring together with N in the formula.

As favorable examples of $(R^1)_4N^+$ include, ammonium, trimethylammonium, tetramethylammonium, triethylammonium, tributylammonium, tetrabutylammonium, trioctylammonium, anilinium, 2,6-dimethylanilinium, N,N-dimethylanilinium, benzyltrimethylammonium, benzyltriethylammonium, benzyltripropylammonium, N-benzyl-N,N-dimethylanilinium, and N-(p-methoxy)benzyl-N,N-dimethylanilinium, but are not particularly limited thereto.

Note that the resist lower-layer composition is desired to include the thermal acid generator which generates acid only upon heating, as described above. For this stability, its thermal decomposition starting temperature, i.e., thermal acid generating temperature, is 100° C. or higher, preferably 150° C. or higher. Note that thermal decomposition starting temperatures are typically 300° C. or lower.

To control the thermal decomposition starting temperatures, it is preferable to select an ammonium cation $(R^1)_4N^+$. In the case of salts other than quaternary ammonium salts, stronger basicities of conjugate bases of the salts lead to more stabilities in many cases. Further, N-benzyl-N,N-dimethylanilinium or the like is relatively low in thermal stability.

Here, there will be described a synthetic method of an onium salt represented by the general formula (2), as one of the thermal acid generators of the present invention for generating the acid represented by the general formula (1).

Firstly, 2-bromo-2,2-difluoroethanol and carboxylic chloride are reacted with each other to obtain 2-bromo-2,2-difluoroethylalkane carboxylate or 2-bromo-2,2-difluoroethylarene carboxylate, then the bromo group is turned to sodium sulfinate by a sulfur compound such as sodium dithionite, and then the sulfinic acid is converted into sulfonic acid by an oxidizing agent such as hydrogen peroxide (the following reaction formula 1).

reaction formula 1

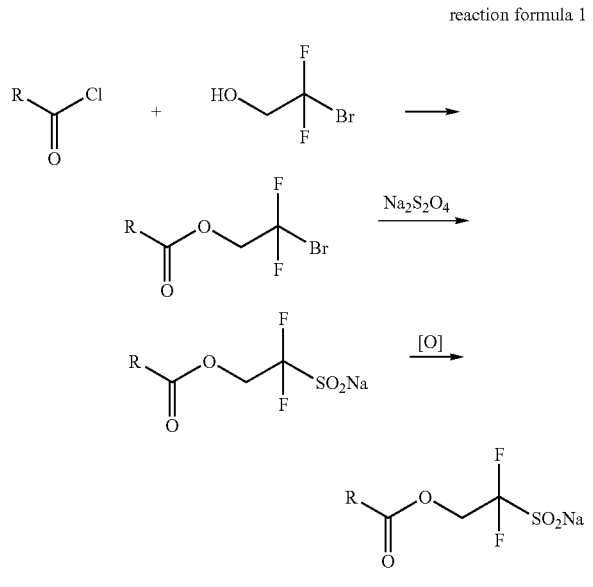

wherein R represents the same meanings as before.

Although the esterification, the conversion from the halogenated alkane into the sodium sulfinate, and the conversion into sulfonic acid are well known, the latter two procedures are detailed in the Japanese Patent Laid-Open (kokai) No. 2004-2252 and the like.

Next, the intended onium salt can be obtained by an ion-exchange reaction between the obtained sodium sulfonate and an onium salt compound (the following reaction formula 2). The ion-exchange reaction is detailed in Japanese Patent Laid-Open (kokai) No. 2007-145797 or the like. Anion exchange can be conducted in alcohol-based solvents such as methanol and ethanol, and a two-layer system of dichloromethane-water or the like. Alternatively, as described in Japanese Patent Laid-Open (kokai) No. 2002-167340, it is possible to adopt a procedure to react a corresponding methyl sulfonate ester with sulfonium halide or iodonium halide to remove a halogenide ion as a methyl halogenide, to conduct an anion exchange with methyl sulfate.

reaction formula 2

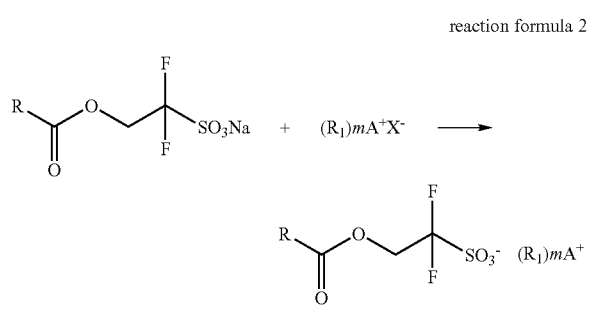

wherein, R, R$^1$, m, and A represent the same meanings as before; and

X$^-$ represents an anion such as a chloride ion, bromide ion, hydrogensulfate anion, acetate, or the like, which is ion-exchangeable with an applicable sulfonic acid.

As described above, the thermal acid generator represented by an onium salt, oxime, and imide each having 1,1-difluoro-2-acyloxyethane-1-sulfonate for generating the acid represented by the general formula (1), can be prepared by adopting industrially available 2-bromo-2,2-difluoroethanol.

Further, the acyl group represented by RCO— as introduced in the above manner can be acylated again, after ester hydrolysis or solvolysis. The outline of the process is shown by the following reaction formula 3.

reaction formula 3

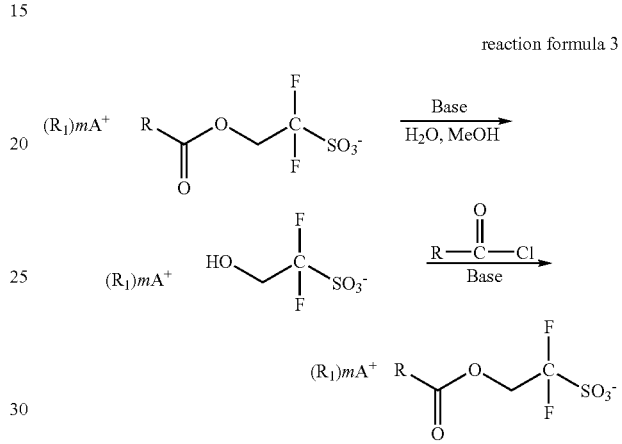

wherein, R, R$^1$, m, and A represent the same meanings as before.

By this procedure, it is possible to introduce an unstable substitutional group under the previous condition upon anion synthesis (where a bromo group is turned to sodium sulfinate by a sulfur compound such as sodium dithionite, and then the sulfinic acid is converted into sulfonic acid by an oxidizing agent such as hydrogen peroxide).

As described above, the sulfonic acid represented by the formula (1) has an ester site which is alkaline hydrolyzable, so that the sulfonic acid can be converted into compounds having lower molecular weights and lower accumulative properties; and the fluorine substitution rate of the sulfonic acid is low, so that it exhibits a higher combustibility even upon disposal by combustion; resulting in a lower load to the environment, unlike PFOS's.

Further, since the sulfonic acid represented by the general formula (1) has an ester site within the molecule in this way, it is easy to introduce thereinto an unbulky acyl group or bulky acyl group, benzoyl group, naphthoyl group, anthrayl group, as well as a polar group, thereby allowing for a wider freedom of molecular design.

The sulfonium salt, iodonium salt, and the like as the source materials can be synthesized by referring to "The Chemistry of sulfonium group Part 1", chap. 11, 267-312, John-Wiley & Sons (1981), "Advanced Photochemistry", vol. 17, 313-355, John-Wiley & Sons (1992), "J. Org. Chem.", 1988.53. 5571-5573, or Japanese Patent Laid-Open (kokai) No. 8-311018, Japanese Patent Laid-Open (kokai) No. 9-15848, Japanese Patent Laid-Open (kokai) No. 2001-122850, Japanese Patent Laid-Open (kokai) No. 7-25846, Japanese Patent Laid-Open (kokai) No. 2001-181221, Japanese Patent Laid-Open (kokai) No. 2002-193887, Japanese Patent Laid-Open (kokai) No. 2002-193925, and the like. Further, the onium cation having an acryloyloxy group or methacryloyloxy as a polymerizable substitutional group can be synthesized by reacting an existing hydroxyphenyldiphenylsulfonium halide with acryloyl chloride or methacryloyl chloride under a basic condition by a method described in Japanese Patent Laid-Open (kokai) No. 4-230645, Japanese Patent Laid-Open (kokai) No. 2005-84365, and the like.

Note that the oxime sulfonate, imide sulfonate, and the like can be prepared by appropriately converting the aforementioned sodium sulfonate salt into an acid halide or acid anhydride, followed by reaction with N-hydroxydicarboimide or oxime. The synthesis of imide sulfonate, oxime sulfonate, and the like can be achieved by referring to the aforementioned Japanese Patent Laid-Open (kokai) No. 2003-252855, U.S. Pat. No. 6,261,738, Japanese Patent Laid-Open (kokai) No. 9-95479, Japanese Patent Laid-Open (kokai) No. 9-208554, Japanese Patent Laid-Open (kokai) No. 9-230588, Japanese Patent No. 2906999, Japanese Patent Laid-Open (kokai) No. 9-301948, Japanese Patent Laid-Open (kokai) No. 2000-314956, Japanese Patent Laid-Open (kokai) No. 2001-233842, WO2004/074242 and the like.

The preferable content of the thermal acid generator represented by the general formula (2) or general formula (3) in the resist lower-layer composition of the present invention is desirably 0.1 to 50 mass parts relative to 100 mass parts of the polymer (base resin) in the resist lower-layer composition. This is because, the thermal acid generator within this range is higher in ability to neutralize amine contaminants brought about from a substrate, thereby enabling to further reduce adverse effects such as footing of a resist pattern. Further, contents less than 0.1 mass part lead to insufficient crosslinking of an applicable film to possibly cause mixing thereof with a resist film or intermediate film acting as an overlying layer, and contents exceeding 50 mass parts may cause cracks in an applicable film.

The present invention firstly provides a resist lower-layer composition characterizedly comprising, as a thermal acid generator, the thermal acid generator for generating the sulfonic acid represented by the general formula (1), the acid crosslinking agent, and the base resin. The present invention secondly provides a substrate having a resist lower layer film formed by using the above-described resist lower-layer composition, and thirdly provides a patterning process adopting the above-described resist lower-layer composition.

Here, the resist lower-layer composition of the present invention contains:

(A) a thermal acid generator for generating a sulfonic acid represented by the above-described general formula (1), such as an onium salt represented by the above-described general formula (2) or an ammonium salt represented by the above-described general formula (3);

(B) a base resin; and (C) an acid crosslinking agent; and if required, (D) an organic solvent; and (E) a surfactant; and if further required, (F) an acid generator for generating an acid other than the sulfonic acid represented by the above-described general formula (1); and (G) a basic compound for improving a storage stability.

Examples of the base resin (B) to be used in the resist lower-layer composition of the present invention include a resin characterizedly containing a silicon atom, and a resin characterizedly containing none of a silicon atom, titanium atom, and germanium atom, but containing carbons in an amount of 50 mass % or more.

Examples of the resin characterizedly containing none of a silicon atom, titanium atom, and germanium atom, but containing carbons in an amount of 50 mass % or more, include polymers of monomers having a polymerizable unsaturated bond, such as styrene derivatives, indene, indole, methyleneindan, acenaphthylene, (meth)acryl derivatives, norbornadiene derivatives, norbornene derivatives, maleic anhydride, maleimide derivatives, vinylnaphthalene derivatives, vinylanthracene derivatives, vinyl ether derivatives, allyl ether derivatives, (meth)acrylonitrile, vinyl pyrrolidone, and vinyl carbazole. Note that (meth)acryl means methacryl and/or acryl.

Next, examples of the resin include novolak resins obtained by condensing phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-t-butylphenol, 3-t-butylphenol, 4-t-butylphenol, resorcinol, 2-methylresorcinol, 4-methylresorcinol, 5-methylresorcinol, catechol, 4-t-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-t-butyl-5-methylphenol, pyrogallol, thymol, 1-naphthol, 2-naphthol, 2-methyl-1-naphthol, 4-methoxy-1-naphthol, 7-methoxy-2-naphthol, dihydroxynaphthalenes such as 1,5-dihydroxynaphthalene, 1,7-dihydroxynaphthalene, and 2,6-dihydroxynaphthalene, methyl 3-hydroxy-naphthalene-2-carboxylate, indene, hydroxyanthracene, acenaphthylene, biphenyl, bisphenol, trisphenol, isothymol, dicyclopentadiene, bicyclo[4.3.0]-nona-3,7-diene, 4-vinylcyclohexene, norbornadiene, 5-vinylnorborna-2-ene, α-pinene, β-pinene, limonene, polyindene, polyacenaphthylene, polystyrene, 9,9-bis(4-hydroxyphenyl)fluorene, 9,9-bis(4-hydroxy-2-methylphenyl)fluorene, 9,9-bis(2-fluoro-4-hydroxyphenyl)fluorene, 9,9-bis(4-hydroxy-2-methoxyphenyl)fluorene, 9,9-bis(4-hydroxy-2-biphenyl)fluorene, 2,2',3,3'-tetrahydro-6,6'-dihydroxy-1,1'-spirobiindene, 2,2',3,3'-tetrahydro-6,6'-dihydroxy-3,3,3',3'-tetramethyl-1,1'-spirobiindene; with aldehydes.

Here, aldehydes are not necessarily required, in case of cocondensation of dicyclopentadiene, bicyclo[4.3.0]-nona-3,7-diene, 4-vinylcyclohexene, norbornadiene, 5-vinylnorborna-2-ene, α-pinene, β-pinene, limonene or the like, with phenols. More concrete examples thereof include resins such as cresol novolak, naphthol novolak, bisphenolfluorene novolak, phenoldicyclopentadiene novolak, naphtholdicyclopentadiene novolak, amorphous carbon, polyhydroxy styrene, acenaphthylene-based polymer, (meth)acrylate, polyimide, and polysulfone. Further, it is also possible to use those materials described in Japanese Patent Laid-Open (kokai) No. 2005-15532, Japanese Patent Laid-Open (kokai) No. 2004-205685, Japanese Patent Laid-Open (kokai) No. 2004-354554, Japanese Patent Laid-Open (kokai) No. 2005-128509, Japanese Patent Laid-Open (kokai) No. 2005-84621, Japanese Patent Laid-Open (kokai) No. 2006-53543, Japanese Patent Laid-Open (kokai) No. 2006-126301, Japanese Patent Laid-Open (kokai) No. 2006-227391, Japanese Patent Laid-Open (kokai) No. 2006-259249, Japanese Patent Laid-Open (kokai) No. 2006-259482, Japanese Patent Laid-Open (kokai) No. 2006-285095, Japanese Patent Laid-Open (kokai) No. 2006-293207, Japanese Patent Laid-Open (kokai) No. 2006-293298, Japanese Patent Laid-Open (kokai) No. 2007-17949, Japanese Patent Laid-Open (kokai) No. 2007-17950, Japanese Patent Laid-Open (kokai) No. 2007-140461, Japanese Patent Laid-Open (kokai) No. 2007-171895, Japanese Patent Laid-Open (kokai) No. 2007-199653, Japanese Patent Laid-Open (kokai) No. 2007-316188, Japanese Patent Laid-Open (kokai) No. 2007-316282, Japanese Patent Laid-Open (kokai) No. 2008-26600, Japanese Patent Laid-Open (kokai) No. 2008-39811, Japanese Patent Laid-Open (kokai) No. 2008-65303, and Japanese Patent Laid-Open (kokai) No. 2008-96684.

As a silicon-containing intermediate layer in a three-layer resist method, an intermediate layer based on polysilsesquioxane is preferably used. By causing the intermediate layer to possess an effect as an antireflective film, reflection can be restricted. Particularly, although a k value is increased and thus substrate reflection is increased in case of adopting a composition as a resist lower layer film for 193 nm exposure, which composition contains many aromatic groups and is high in resistance to substrate etching, the substrate reflection can be limited to 0.5% or less by restricting the reflection by virtue of the intermediate layer.

Preferably usable as an intermediate layer possessing an antireflective effect, are anthracene for 248 nm, 157 nm exposure, and polysilsesquioxane having a pendant phenyl group or a pendant light-absorbing group including a silicon-silicon bond for 193 nm exposure (Japanese Patent Laid-Open (kokai) No. 2004-341479). Note that it is possible to preferably adopt those silicon-containing polymer compounds each containing a crosslinkable substitutional group such as an epoxy group (Japanese Patent Laid-Open (kokai) No. 2005-48152, Japanese Patent Laid-Open (kokai) No. 2004-310019, Japanese Patent Laid-Open (kokai) No. 2005-18054, Japanese Patent Laid-Open (kokai) No. 2005-352104, Japanese Patent Laid-Open (kokai) No. 2007-65161, Japanese Patent Laid-Open (kokai) No. 2007-163846, Japanese Patent Laid-Open (kokai) No. 2007-164148, Japanese Patent Laid-Open (kokai) No. 2007-146149, Japanese Patent Laid-Open (kokai) No. 2007-226170, Japanese Patent Laid-Open (kokai) No. 2007-226204, Japanese Patent Laid-Open (kokai) No. 2008-81646, and Japanese Patent Laid-Open (kokai) No. 2008-836.68).

Further, examples of the (C) component, i.e., the acid crosslinking agent for forming a cross-linked structure by an action of acid, include melamine compounds, guanamine compounds, glycoluryl compounds or urea compounds, epoxy compounds, thio-epoxy compounds, isocyanate compounds, azide compounds, and compounds each including a double bond such as an alkenyl ether group, the compounds each being substituted with at least one group selected from a methylol group, alkoxymethyl group, and acyloxymethyl group. Although these may be each used as an additive, they may be each introduced into a polymer side-chain as a pendant group. Further, compounds each including a hydroxy group may also be used as the crosslinking agent.

Among the above-mentioned compounds, examples of epoxy compounds include tris(2,3-epoxypropyl)isocyanurate, trimethylolmethane-triglycidyl ether, trimethylolpropane-triglycidyl ether, and triethylolethane-triglycidyl ether. Concrete examples of melamine compounds exemplarily include: hexamethylol melamine; hexamethoxymethyl melamine; compounds each obtained by methoxy-methylating 1 to 6 methylol groups of hexamethylol melamine, or mixtures of the compounds; hexamethoxyethyl melamine; hexaacyloxymethyl melamine; and compounds each obtained by acyloxy-methylating 1 to 6 methylol groups of hexamethylol melamine, or mixtures of the compounds. Examples of guanamine compounds include tetramethylol guanamine; tetramethoxymethyl guanamine; compounds each obtained by methoxy-methylating 1 to 4 methylol groups of tetramethylol guanamine, or mixtures of the compounds; tetramethoxyethyl guanamine; tetraacyloxy guanamine; and compounds each obtained by acyloxy-methylating 1 to 4 methylol groups of tetramethylol guanamine, or mixtures of the compounds. Examples of glycoluril compounds include tetramethylol glycoluril; tetramethoxy glycoluril; tetramethoxymethyl glycoluril; compounds each obtained by methoxy-methylating 1 to 4 methylol groups of tetramethylol glycoluril, or mixtures of the compounds; and compounds each obtained by acyloxy-methylating 1 to 4 methylol groups of tetramethylol glycoluril, or mixtures of the compounds. Examples of urea compounds include tetramethylol urea; tetramethoxymethyl urea; compounds each obtained by methoxy-methylating 1 to 4 methylol groups of tetramethylol urea, or mixtures of the compounds; and tetramethoxyethyl urea. Examples of compounds each including an alkenyl ether group include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

When a hydrogen atom of a hydroxy group of a novolak resin having a fluorene or spirobiindene structure is substituted with a glycidyl group, addition of a compound including a group where a hydroxy group or a hydrogen atom of hydroxy group is substituted with a glycidyl group, is effective. Particularly preferable are those compounds each including two or more hydroxy groups or glycidyloxy groups in a molecule.

Examples thereof include: alcohol-group containing compounds such as naphtholnovolak, m- and p-cresolnovolak, naphthol-dicyclopentadienenovolak, m- and p-cresol-dicyclopentadienenovolak, 4,8-bis(hydroxymethyl)tricyclo[5.2.1.0$^{2,6}$]-decane, pentaerythritol, 1,2,6-hexanetriol, 4,4',4''-methylidenetriscyclohexanol, 4,4'-[1-[4-[1-(4-hydroxycyclohexyl)-1-methylethyl]phenyl]ethylidene]-biscyclohexanol, [1,1'-bicyclohexyl]-4,4'-diol, methylene-biscyclohexanol, decahydronaphthalene-2,6-diol, [1,1'-bicyclohexyl]-3,3',4,4'-tetrahydroxy; low-nuclear phenol compounds such as bisphenol, methylene-bisphenol, 2,2'-methylene-bis[4-methylphenol], 4,4'-methylidene-bis[2,6-dimethylphenol], 4,4'-(1-methyl-ethylidene)bis[2-methylphenol], 4,4'-cyclohexylidene-bisphenol, 4,4'-(1,3-dimethylbutylidene)bisphenol, 4,4'-(1-methylethylidene)-bis[2,6-dimethylphenol], 4,4'-oxybisphenol, 4,4'-methylene-bisphenol, bis(4-hydroxyphenyl)methanone, 4,4'-methylene-bis[2-methylphenol], 4,4'-[1,4-phenylene-bis(1-methylethylidene)]bisphenol, 4,4'-(1,2-ethanediyl)bisphenol, 4,4'-(diethylsilylene)bisphenol, 4,4'-[2,2,2-trifluoro-1-(trifluoro methyl)ethylidene]bisphenol, 4,4',4''-methylidene-trisphenol, 4,4'-[1-(4-hydroxyphenyl)-1-methylethyl]phenyl]ethylidene]-bisphenol, 2,6-bis[(2-hydroxy-5-methylphenyl)methyl]-4-methylphenol, 4,4',4''-ethylidyne-tris[2-methylphenol], 4,4',4''-ethylidyne-trisphenol, 4,6-bis[(4-hydroxyphenyl)methyl]-1,3-benzenediol, 4,4'-[(3,4-dihydroxyphenyl)methylene]-bis[2-methylphenol], 4,4',4'',4'''-(1,2-ethanediylidene)tetrakisphenol, 4,4',4'',4'''-ethanediylidene)tetrakis[2-methylphenol], 2,2'-methylene-bis[6-[(2-hydroxy-5-methylphenyl)methyl]-4-methylphenol], 4,4',4'',4'''-(1,4-phenylenedimethylidyne)tetrakisphenol, 2,4,6-tris(4-hydroxyphenylmethyl)1,3-benzenediol, 2,4',4''-methylidenetrisphenol, 4,4',4''-(3-methyl-1-propanyl-3-ylidene)trisphenol, 2,6-bis[(4-hydroxy-3-fluorophenyl)methyl]-4-fluorophenol, 2,6-bis[4-hydroxy-3-fluorophenyl]methyl-4-fluorophenol, 3,6-bis[(3,5-dimethyl-4-hydroxyphenyl)methyl]-1,2-benzenediol, 4,6-bis[(3,5-dimethyl-4-hydroxyphenyl)methyl]-1,3-benzenediol, p-methylcalix[4]arene, 2,2'-methylene-bis[6-[(2,5/3,6-dimethyl-4/2-hydroxyphenyl)methyl]-4-methylphenol, 2,2'-methylenebis[6-[(3,5-dimethyl-4-hydroxyphenyl)methyl]-4-methylphenol, 4,4',4'',4'''-tetrakis[(1-methylethylidene)bis(1,4-cyclohexylidene)]phenol, 6,6'-methylenebis[4-(4-hydroxyphenylmethyl)-1,2,3-benzenetriol, 3,3',5,5'-tetrakis[(5-methyl-2-hydroxyphenyl)methyl]-[(1,1'-biphenyl)-4,4'-diol]; or compounds each obtained by glycidyl-etherifying a hydroxy group(s) of the above compounds.

The blending amount of the crosslinking agent in the present invention is preferably 5 to 50 parts, particularly preferably 10 to 40 parts, relative to 100 parts of the resin. Blending amounts less than 5 parts occasionally cause mixing of the film with a resist, and blending amounts exceeding 50 parts occasionally lead to deteriorated antireflective effects, and occurrences of cracks in the film after cross-linking. These crosslinking agents may be used singly, or in a combination of two or more kinds.

Usable as (D) an organic solvent in the present invention are any organic solvents in which the base resin(s), the thermal acid generator, the acid crosslinking agent, other additives, and the like are soluble. Examples of the organic solvents include: ketones such as cyclohexanone and methyl-2-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-methyl ether acetate and propylene glycol mono-tert-butyl ether acetate, without limited thereto. Desirably usable in the present invention among them, are diethylene glycol dimethyl ether, 1-ethoxy-2-propanol, ethyl lactate, propylene glycol monomethyl ether acetate, propylene glycol monomethyl ether, and mixed solvents of them.

The usage amount of the organic solvent is preferably 200 to 10,000 parts, and particularly 300 to 5,000 parts relative to 100 parts of the above-mentioned base resin.

Examples of surfactants (E) used in present invention include, without particular limitation, polyoxyethylene alkyl ethers such as polyoxyethylene lauryl ether, polyoxyethylene stearyl ether, polyoxyethylene cetyl ether, and polyoxyethylene olein ether;

polyoxyethylene alkyl alyl ethers such as polyoxyethylene octyl phenol ether, and polyoxyethylene nonyl phenol ether;

polyoxyethylene polyoxypropylene block copolymers;

sorbitan fatty acid esters such as sorbitan monolaurate, sorbitan monopalmitate, and sorbitan monostearate;

nonionic surfactants of polyoxyethylene sorbitan fatty acid ester, such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate;

fluorinated surfactants such as F TOP EF301, EF303, EF352 (produced by JEMCO Inc.), MEGAFAC F171, F172, F173, R08, R30, R90, R94 (produced by Dai-Nippon Ink & Chemicals, Inc.), Fluorad FC-430, FC-431, FC-4430, FC-4432 (produced by Sumitomo 3M Co., Ltd.), ASAHI-GUARD AG710, SURFLON S-381, S-382, SC101, SC102, SC103, SC104, SC105, SC106, SURFINOL E1004, KH-10, KH-20, KH-40 (produced by Asahi Glass Co.,);

organosiloxane polymers KP341, X-70-092, X-70-093 (produced by Shin-Etsu Chemical Co., Ltd.); and acrylic or methacrylic POLYFLOW No. 75, No. 95 (produced by Kyoeisha Yushi Kagaku Kogyo Co., Ltd.); and those surfactants are also preferably used, which are partially fluorinated oxetane ring-opening polymers represented by following (surf-1):

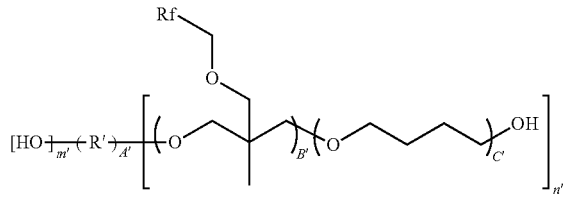

(surf-1)

R' represents an aliphatic group having valence of 2 to 4 and having 2 to 5 carbon atoms, and concrete examples thereof include: 1,4-butylene, 1,2-propylene, 2,2-dimethyl-1,3-propylene, 1,5-pentylene as divalent ones; and those represented by the following formulae, as trivalent and tetravalent ones:

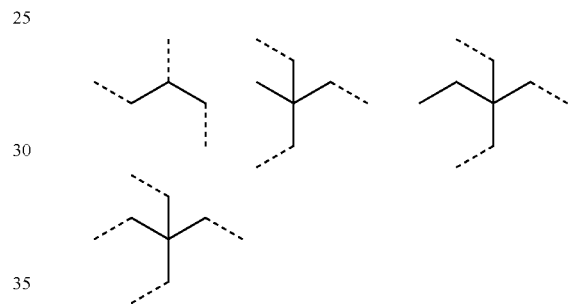

wherein broken lines represent bonding hands, and the structures are partial ones derived from glycerol, trimethylolethane, trimethylolpropane, and pentaerythritol, respectively.

Rf is a trifluoromethyl group or pentafluoroethyl group, and the trifluoromethyl group is preferable. m' is an integer of 0 to 3, n' is an integer of 1 to 4, and the sum of n' and m' indicates a valence of R' and is an integer of 2 to 4. A' is 1, B' represents an integer of 2 to 25, and C' represents an integer of 0 to 10. Preferably, B' represents an integer of 4 to 20, and C' represents an integer of 0 to 1. Further, constitutional units in the above structures do not define the order of them, and may be bonded in a block or random manner. Production of surfactants based on partially fluorinated oxetane ring-opening polymers, is detailed in U.S. Pat. No. 5,650,483. Desirable among them are, FC-4430, SURFLON S-381, SURFINOL E1004, KH-20, KH-30, and the oxetane ring-opening polymers represented by the structural formula. These can be used solely, or mixedly in two or more kinds.

The addition amount of the surfactant in the resist lower-layer composition of the present invention is 2 parts or less, preferably 1 part or less, relative to 100 parts of the resin.

Examples of the acid generator for generating an acid other than the sulfonic acid represented by the above-described general formula (1) include: acid generators such as sulfonium salts, iodonium salts, diazomethane derivatives, and the like enumerated in Japanese Patent Laid-Open (kokai) No. 2005-128509; and acid generators for generating partially fluorinated alkane sulfonic acids described in the above-mentioned Japanese translation of PCT international application No. 2004-531749, Japanese Patent Laid-Open (kokai) No. 2004-2252, and Japanese Patent Laid-Open (kokai) No. 2002-214774. As previously noted, since known photoacid generators are configured to generate acids not only by irradiation of high-energy beams but also by heating, any one of the existing photoacid generators can be used as the acid generator for generating an acid other than the sulfonic acid represented by the above-described general formula (1).

Although the addition amount of the component(s) (F) is arbitrary insofar as the effect of the component (A) is not obstructed, the addition amount is to be 10 parts or less, and preferably 5 parts or less relative to 100 parts of the resin.

The basic compound as the component (G) for improved stability plays a role of quencher against an acid in a small amount generated by the acid generator, in a manner to prevent progression of a cross-linking reaction by the acid.

Examples of such a basic compound include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group; alcoholic nitrogen-containing compounds, amide derivatives, imide derivatives, and the like. More concretely, those basic compounds enumerated in Japanese Patent Laid-Open (kokai) No. 2005-128509 are usable.

Although the addition amount of the component (G) is arbitrary insofar as the effect of the component (A) is not obstructed, the addition amount is to be 0.001 to 2 parts, and particularly preferably 0.01 to 1 part relative to 100 parts of the resin. Blending amounts less than 0.001 part lead to no addition effects, and addition amounts exceeding 2 parts may lead to trapping of all of generated acids to possibly fail to cause cross-linking.

In turn, the resist lower-layer composition of the present invention is used to form a layer lower than a photoresist layer in a multi-layer resist method, and is particularly used to form a resist lower layer film in a two-layer resist method, and an intermediate layer and a resist lower layer film in a three-layer resist method.

Namely, the present invention provides a patterning process for forming a pattern on a substrate by lithography, comprising the steps of: at least, forming a resist lower layer film on a layer to be processed of the substrate, by using the resist lower-layer composition of the present invention;

forming a resist upper layer film on the resist lower layer film by using a photoresist composition, to form at least two multi-layer resist films;

subsequently conducting exposure of a pattern circuit region of the resist upper layer film, developing it by a developer to form a resist pattern in the resist upper layer film, and etching the resist lower layer film by using the thus obtained resist pattern as a mask to form a resist lower layer film pattern; and etching the layer to be processed of the substrate by using the thus obtained resist lower layer film pattern as a mask, to form a pattern on the substrate.

Such a two-layer resist method will be described with reference to FIG. 1.

It is possible to adopt the resist lower-layer composition of the present invention to form a resist lower layer film 2 on a layer to be processed 1b of a substrate 1, such as by spin coating. After formation of the resist lower layer film 2, it is desirable to bake the same so as to evaporate the organic solvent therein, and to promote crosslinking reaction for preventing the film from being mixed with a resist upper layer film 3 to be formed later. Preferably usable baking temperature is within a range of 80 to 400° C. and within a time range of 10 to 300 seconds. Note that the thickness of the resist lower layer film 2 is appropriately selected, and the thickness is preferably 50 to 20,000 nm, and particularly 100 to 15,000 nm. After formation of the resist lower layer film 2, the resist upper layer film 3 is formed thereon (see FIG. 1(a)). Note that the present invention is applied to a situation including a procedure of heating at 100° C. or higher in any one of steps of the multi-layer resist method.

In the two-layer resist method, when the base resin in the resist lower layer film contains none of a silicon atom, titanium atom, and germanium atom, it is possible to preferably use a photoresist composition containing a silicon atom for forming the resist upper layer film 3. In turn, when the base resin in the resist lower layer film contains a silicon atom, it is possible to preferably use a composition containing no silicon atoms for the resist upper layer film. Namely, the etching selectivity ratio can be increased, when one of the composition for the resist lower layer film and the composition for the resist upper layer film contains a silicon atom.

As the silicon-containing photoresist composition for the two-layer resist method, those photoresist compositions of a positive type or the like are each preferably used, which compositions each contain: as a base resin, a polysilsesquioxane derivative, vinylsilane derivative, polyhedral oligomeric silsesquioxane (POSS) pendant (meth)acrylate, or the like from a viewpoint of oxygen gas etching resistance; and an organic solvent, an acid generator, and, as required, a basic compound and the like. These are not particularly limited, and known ones are to be used. In turn, examples of the photoresist composition containing no silicons for the two-layer resist method include those compounds each containing, as a base resin, hydroxystyrene, (meth)acrylate, norbornene-maleic anhydride copolymer, polynorbornene, or metathesis ring-opening polymer.

In the case on forming the resist upper layer film 3 by using the photoresist composition, spin coating is preferably used, similarly to formation of the resist lower layer film 2.

After formation of the resist upper layer film 3 by the photoresist composition, prebaking is to be preferably conducted at 80 to 180° C. within a time range of 10 to 300 seconds. Thereafter, exposure is conducted for a pattern circuit region 4 of the resist upper layer film 3 (see FIG. 1(b)), post-exposure bake (PEB) is conducted preferably at 50 to 150° C., and development is conducted, according to usual manners, respectively, to obtain a resist pattern 3' (see FIG. 1(c)).

Although the thickness of the resist upper layer film 3 is not particularly limited, the thickness is preferably 30 to 500 nm, and particularly 50 to 400 nm. Examples of exposure light include high-energy beams having wavelengths of 300 nm or shorter, concretely, excimer lasers of 248 nm, 193 nm, and 157 nm, soft X-rays of 3 to 20 nm, electron beams, X-rays, and the like.

Used for the development is a puddling method, dipping method, or the like using an alkaline water solution, and particularly preferably used is a puddling method adopting a 2.38 mass % aqueous solution of tetramethylammonium hydroxide, which is preferably conducted at a room temperature within a time range of 10 seconds to 300 seconds, and exemplarily followed by rinsing by pure water, and by drying by spin drying, nitrogen blowing, or the like.

Next, etching of the resist lower layer film 2 is conducted by using the obtained resist pattern 3' as a mask, to thereby obtain a resist lower layer film pattern 2' (see FIG. 1(d)). The etching of the resist lower layer film 2 in the two-layer resist method can be exemplarily conducted by dry etching mainly using an oxygen gas. In the case of the dry etching mainly using an oxygen gas, it is possible to add inert gases such as He and Ar, and CO, $CO_2$, $NH_3$, $SO_2$, $N_2$, and $NO_2$ gases, in addition to the oxygen gas. Particularly, the latter gases are used to protect pattern sidewalls by preventing undercuts of the sidewalls. Further, it is possible to use a hydrogen gas instead of an oxygen gas.

Next, etching of the layer to be processed 1b of the substrate 1 may also be conducted according to a usual manner, exemplarily by etching mainly using a flon-based gas when the layer to be processed 1b of the substrate comprises a low-dielectric insulator film such as $SiO_2$, SiN, SiON, or porous silica, and an etching stop film therefor, or by etching mainly using a chlorine-based or bromine-based gas when the layer to be processed 1b is poly-silicon (p-Si), Al, or W, thereby forming a pattern 1b' in the substrate (see FIG. 1(e)).

In case that the layer to be processed 1b of the substrate is etched by a flon-based gas, the silicon-containing resist of the two-layer resist method is removed simultaneously with substrate processing. In turn, in the case that the substrate is etched by a chlorine-based or bromine-based gas; removal of the silicon-containing resist is required to be separately conducted by dry etching removal by a flon-based gas after substrate processing.

As shown in FIG. 1, the substrate 1 can be divided into the layer to be processed 1b to be subjected to etching, and the fundamental substrate 1a not to be subjected to etching. The layer to be processed 1b may be a part of the substrate itself such as $SiO_2$, SiN, SiON, or the like, or may be a low-dielectric insulator film such as a porous film of silica or the like provided on the substrate as a part of the substrate. The layer to be processed is preferably a low-dielectric film having a specific dielectric constant of 3.5 or less or a nitride film, from a viewpoint to prevent electric leakage among wirings. Examples of low-dielectric films having specific dielectric constants of 3.5 or less include silicas having vacancies (porous silicas). Specific dielectric constants can be measured by an electrostatic capacity method, prove method, and the like. Particularly, a mercury prove method is preferably used, and the measuring method is described in Japanese Patent Laid-Open (kokai) No. 2006-117763 (see its paragraph [0081]).

The thickness of the layer to be processed 1b is selected in consideration of the etching conditions and the like, and is preferably 0.1 to 10 μm.

Meanwhile, the present invention provides a patterning process for forming a pattern on a substrate by lithography, comprising the steps of: at least, forming a resist lower layer film on a layer to be processed of the substrate, by using the resist lower-layer composition of the present invention;

forming an intermediate layer containing a silicon atom on the resist lower layer film;

forming a resist upper layer film on the intermediate layer by using a photoresist composition containing no silicon atoms, to form at least three multi-layer resist films;

subsequently conducting exposure of a pattern circuit region of the resist upper layer film, developing it by a developer to form a resist pattern in the resist upper layer film, and dry etching the intermediate layer by using the thus obtained resist pattern as a mask to form an intermediate layer pattern;

etching the resist lower layer film by using the intermediate layer pattern as a mask, to form a resist lower layer film pattern; and etching the layer to be processed of the substrate by using the thus obtained resist lower layer film pattern as a mask, to form a pattern on the substrate.

Such a three-layer resist method will be described with reference to FIG. 2.

Firstly, the resist lower-layer composition of the present invention is used to form a resist lower layer film 12 on a layer to be processed 11b of a substrate 11, in the same manner as the two-layer resist method.

In the case of the three-layer resist method, the resist lower layer film 12 is preferably configured to contain none of a silicon atom, titanium atom, and germanium atom, and there are subsequently formed thereon an intermediate layer 13 containing silicon, and a single-layer resist containing no silicons (resist upper layer film 14) thereon (see FIG. 2(a)).

The resist upper layer film containing no silicon atoms has an advantage of excellent resolution as compared with those containing silicon atoms. Thus, the pattern to be transferred to the intermediate layer, as well as the pattern to be transferred to the lower layer film by dry etching mainly using an oxygen gas by using the obtained intermediate layer pattern as a mask, can be made to be highly precise. Accordingly, by etching the substrate by using the resist lower layer film having the thus transferred pattern as a mask to form a pattern on the substrate, it is possible to make the pattern formed on the substrate to be more highly precise.

As the base resin intended for a resist lower layer film composition for forming the resist lower layer film 12 in the three-layer resist method, it is possible to preferably use the same as the two-layer resist method which contains none of a silicon atom, titanium atom, and germanium atom. The preferable thickness of the resist lower layer film in the three-layer resist method is the same as the preferable thickness of the resist lower layer film in the two-layer resist method.

As the silicon-containing intermediate layer 13 in the three-layer resist process, it is preferable to use, as the base resin, a silicon-atom-containing polymer such as a polysilsesquioxane derivative, polyhedral oligomeric silsesquioxane (POSS) or the like having a cross-linking group from a viewpoint of oxygen gas etching resistance; and an organic solvent, the thermal acid generator of the present invention for generating the acid represented by the formula (1), if necessary, a crosslinking agent, and the like as required. As the concrete composition of the intermediate layer, the known one described in Japanese Patent Laid-Open (kokai) No. 2004-310019 is usable. In this way, as the intermediate layer, it is possible to use the resist lower-layer composition of the present invention, or an existing silicon-containing intermediate layer.

The intermediate layer 13 is film-formed by spin coating, and cross-linking by baking preferably at 50 to 150° C., similarly to a typical resist lower layer film. The thickness of the intermediate layer 13 is appropriately selected, and preferably within a range of 10 to 1,000 nm, particularly 20 to 500 nm.

As a photoresist composition for forming the resist upper layer film 14 in the three-layer resist method, it is possible to use a known one preferably containing no silicon atoms and comprising hydrocarbons. Although the thickness of the resist upper layer film 14 is not particularly limited, the thickness is preferably within a range of 30 to 500 nm, particularly 50 to 400 nm.

Figure 2:
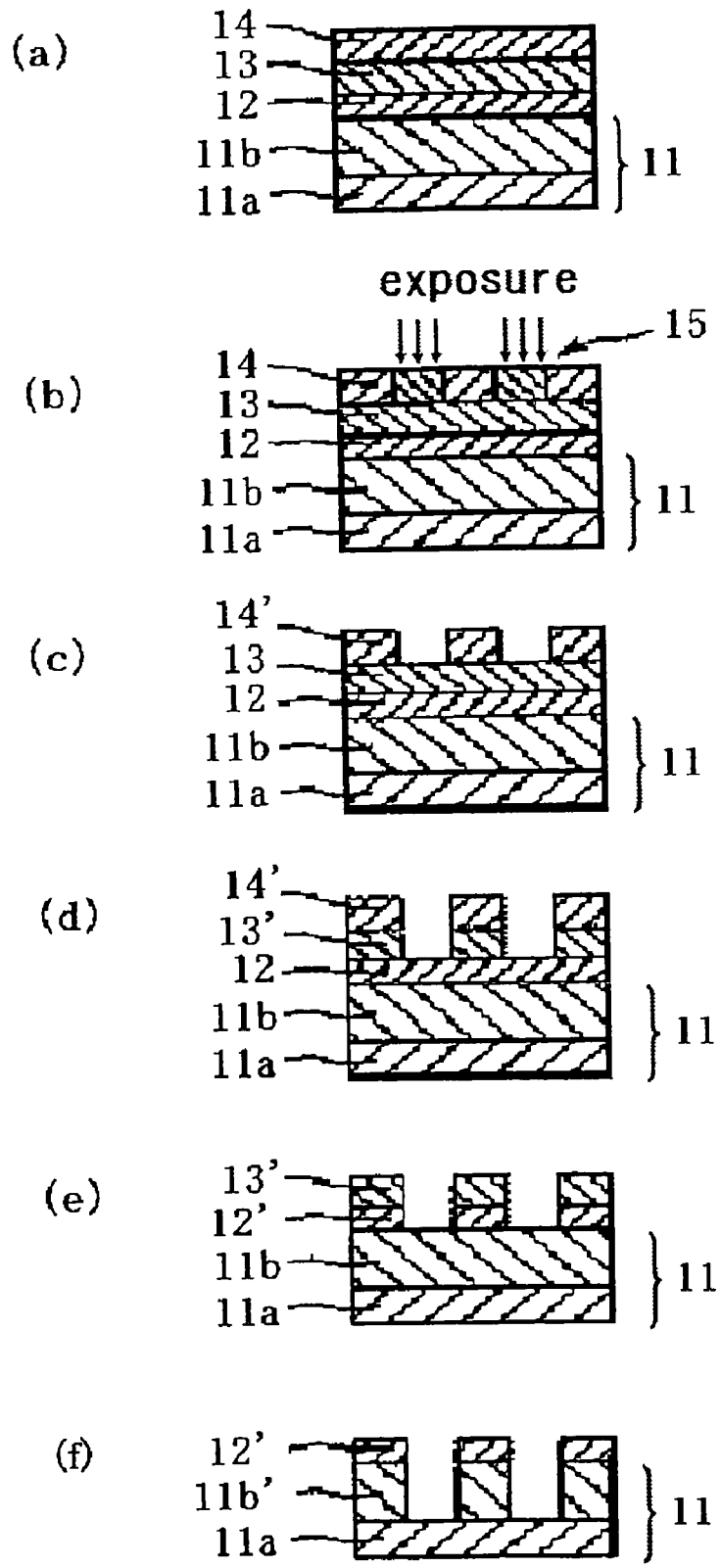
FIG. 2 is an explanatory view of an example of a patterning process of the present invention based on a three-layer resist method.
Figure 3:
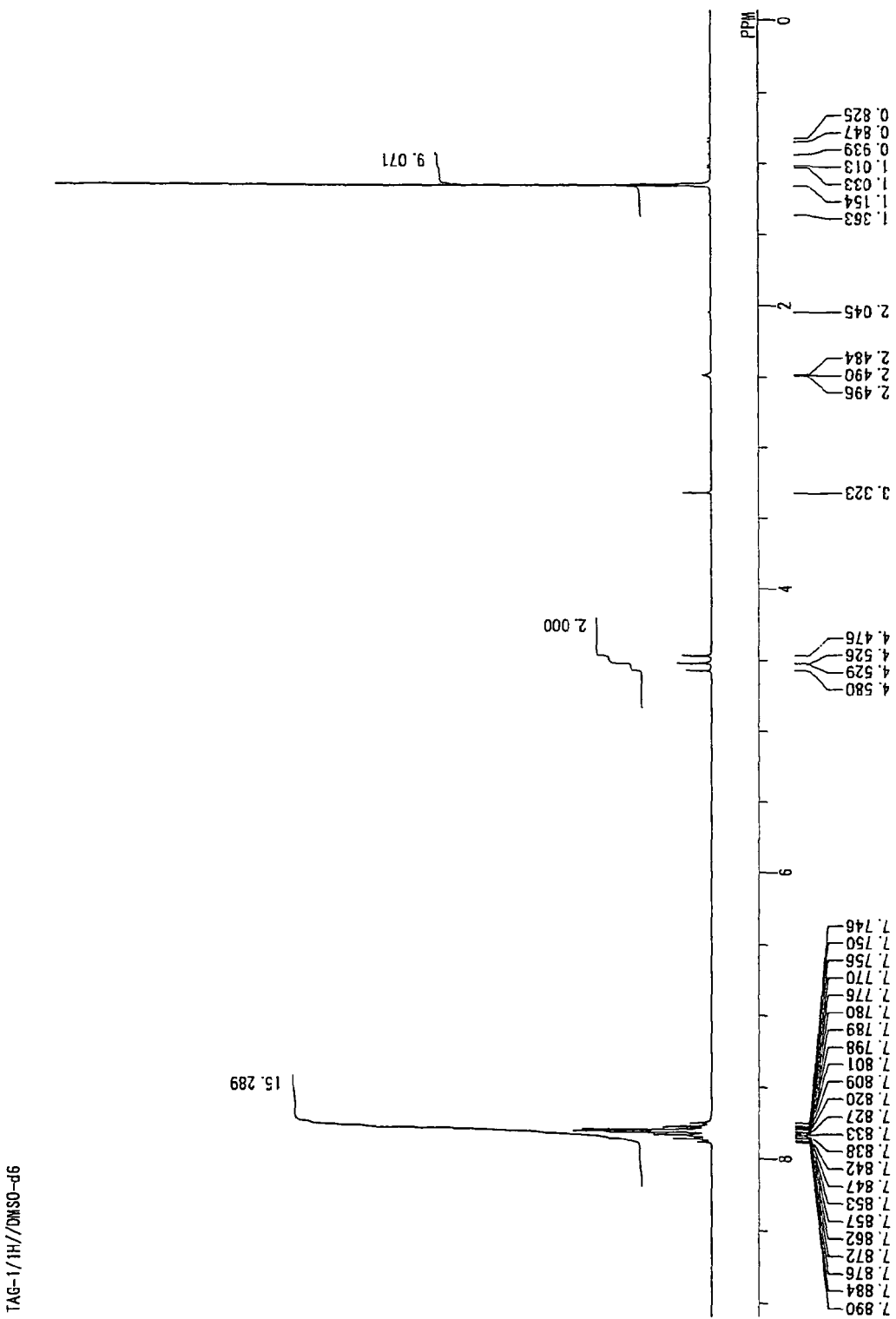
FIG. 3 is a spectrum of $^1$H-NMR/DMSO-$d_6$ of TAG1 in Synthesis Example 5.
Figure 4:
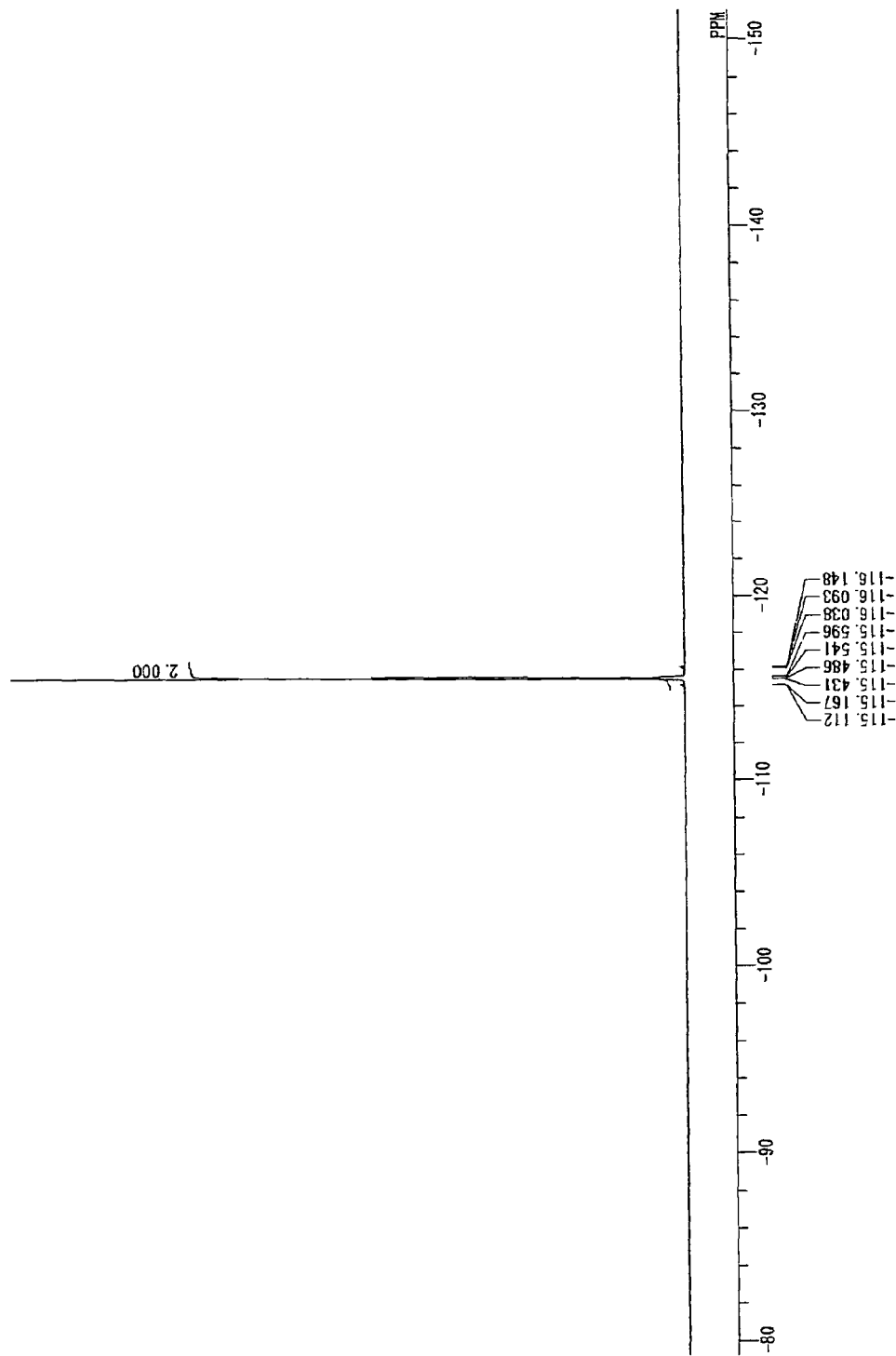
FIG. 4 is a spectrum of $^{19}$F-NMR/DMSO-$d_6$ of TAG1 in Synthesis Example 5.
Figure 5:
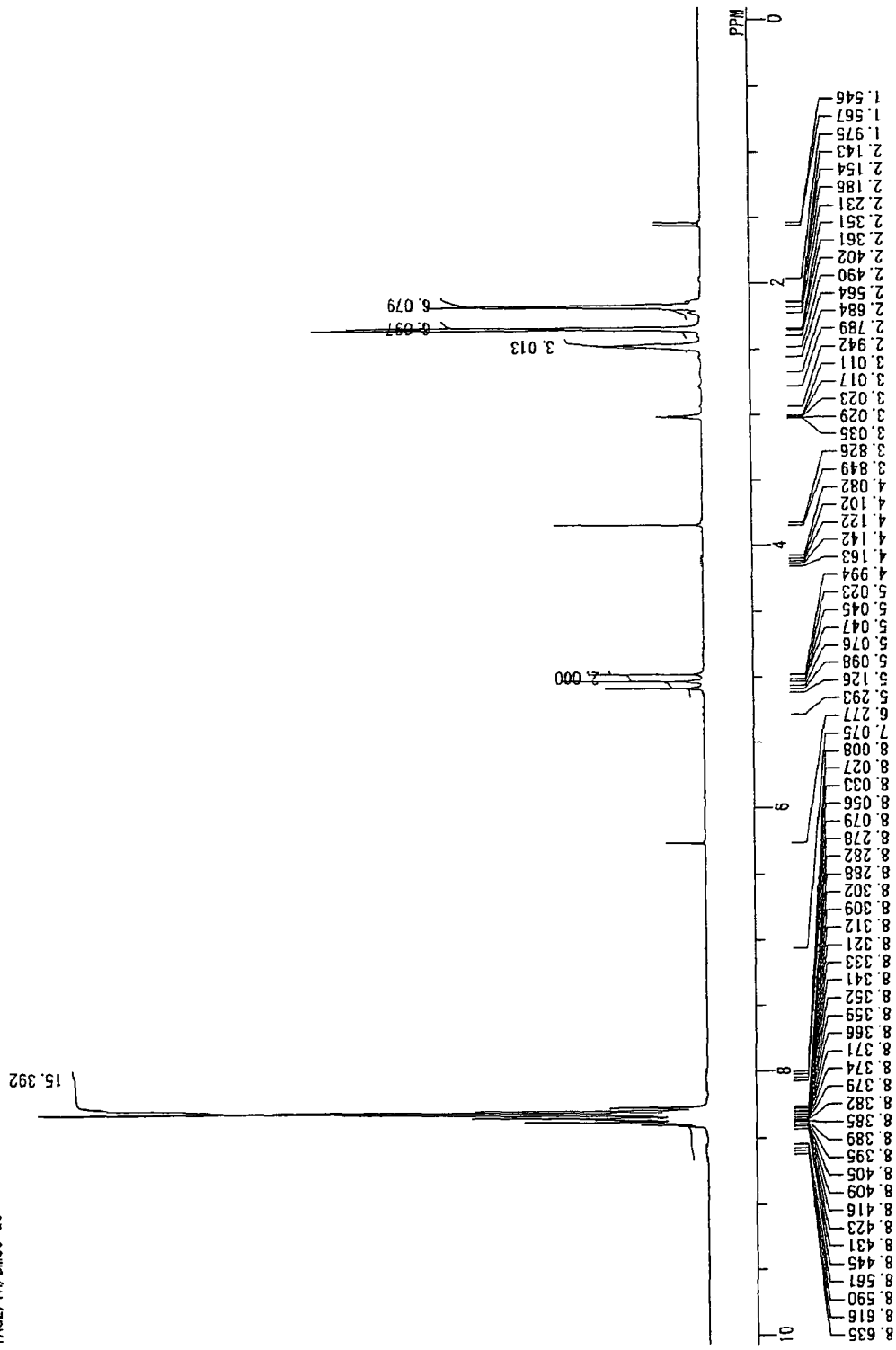
FIG. 5 is a spectrum of $^1$H-NMR/DMSO-$d_6$ of TAG2 in Synthesis Example 6.
Figure 6:
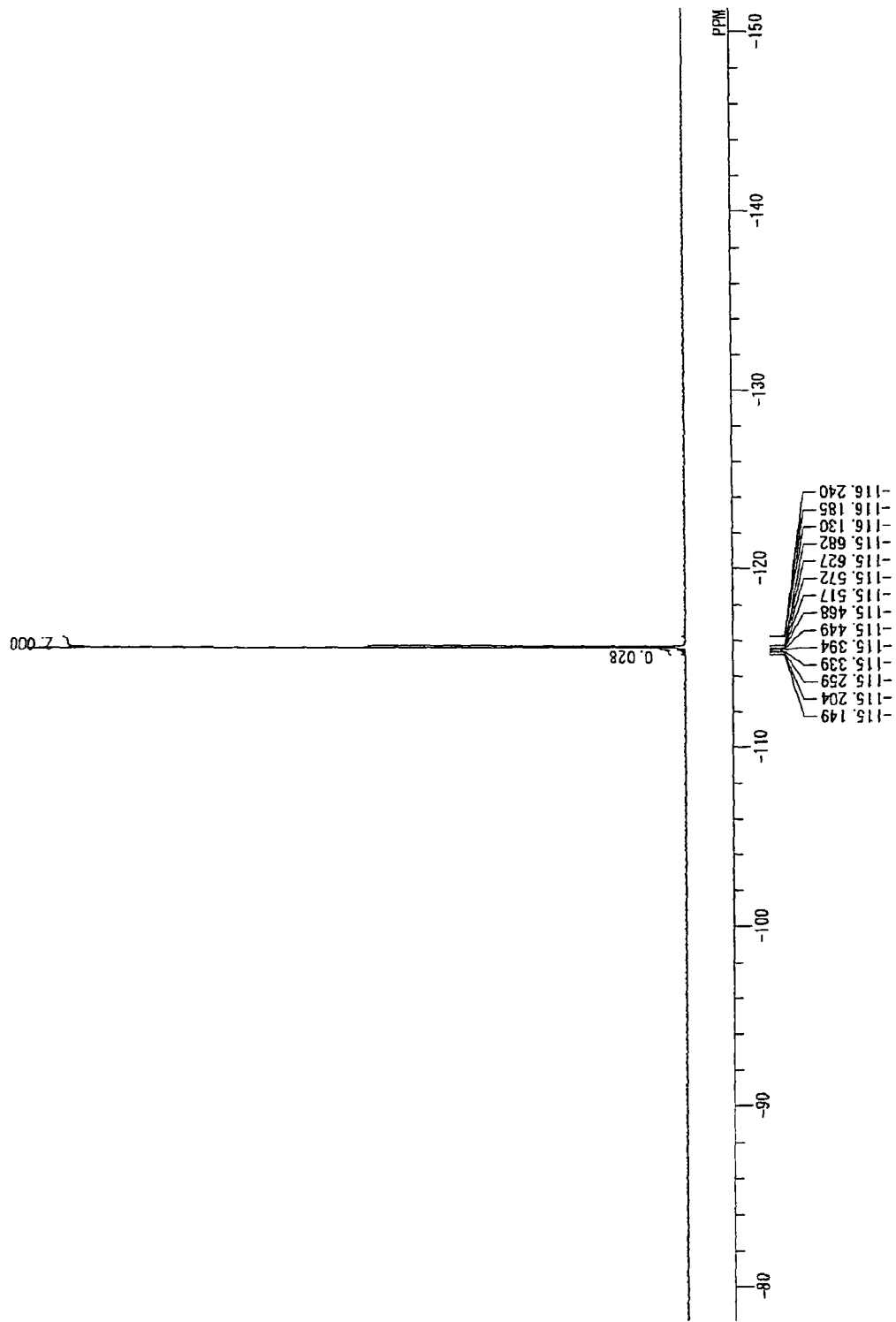
FIG. 6 is a spectrum of $^{19}$F-NMR/DMSO-$d_6$ of TAG2 in Synthesis Example 6.
Figure 7:
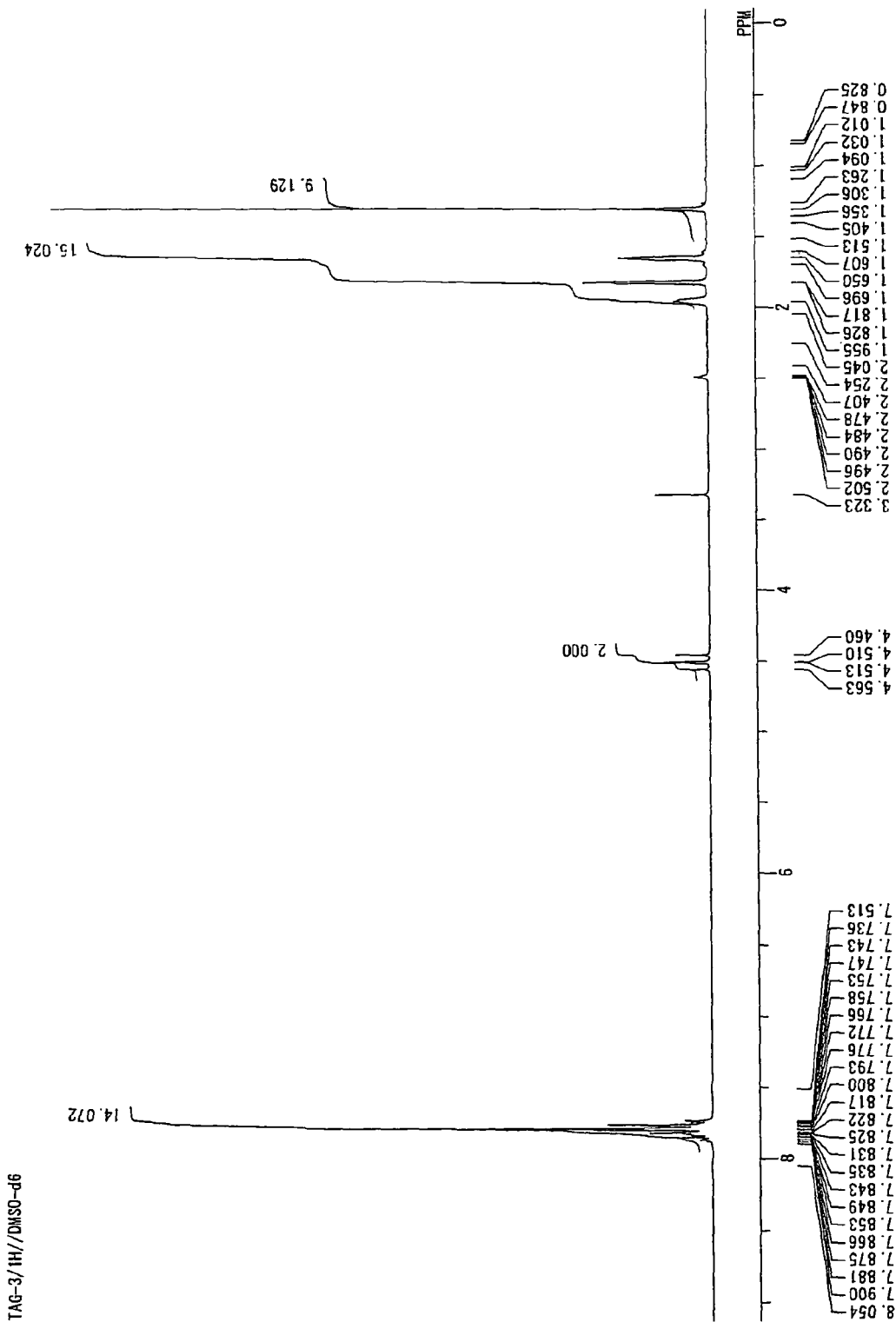
FIG. 7 is a spectrum of $^1$H-NMR/DMSO-$d_6$ of TAG3 in Synthesis Example 7.
Figure 8:
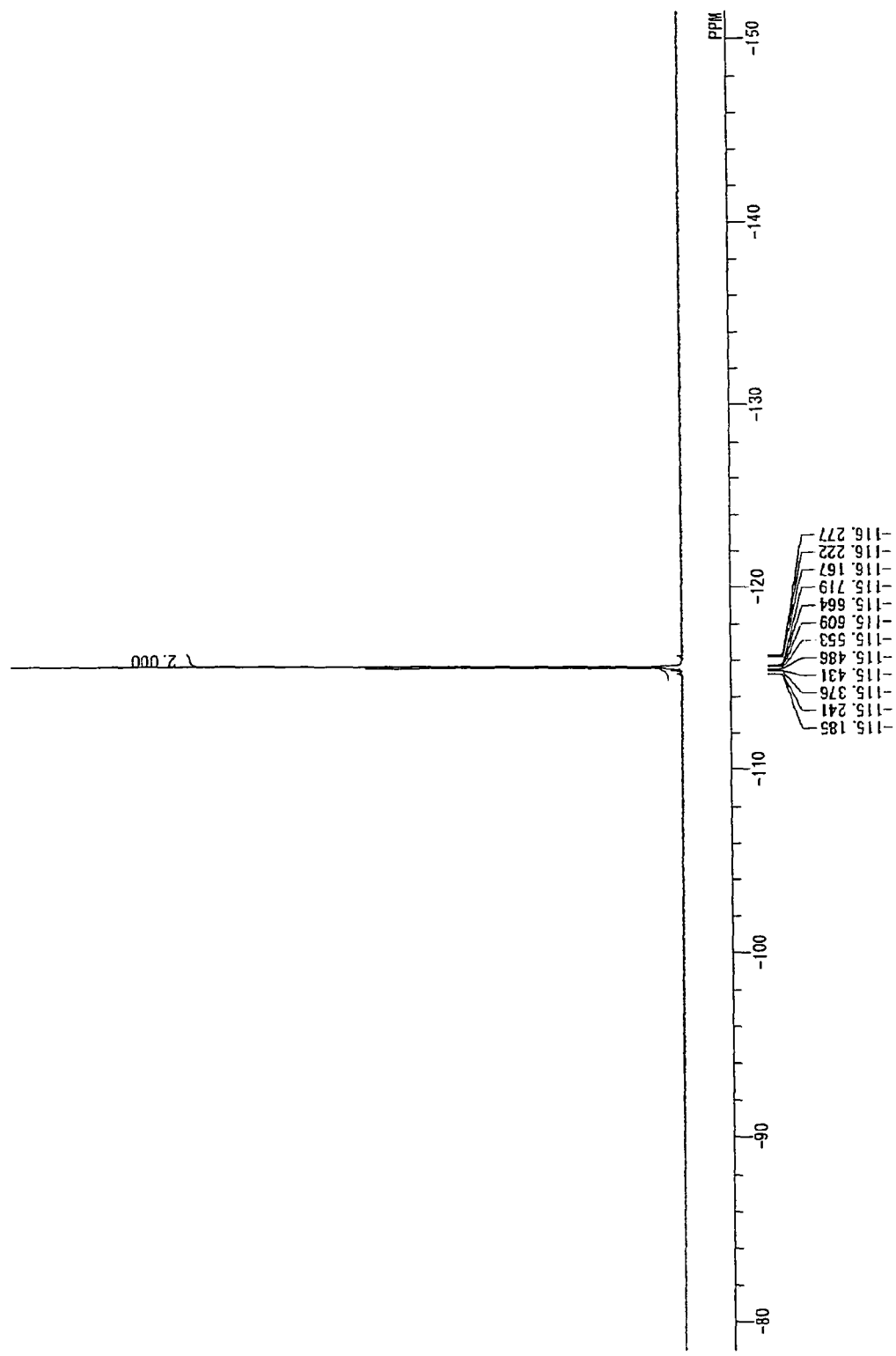
FIG. 8 is a spectrum of $^{19}$F-NMR/DMSO-$d_6$ of TAG3 in Synthesis Example 7.
Figure 9:
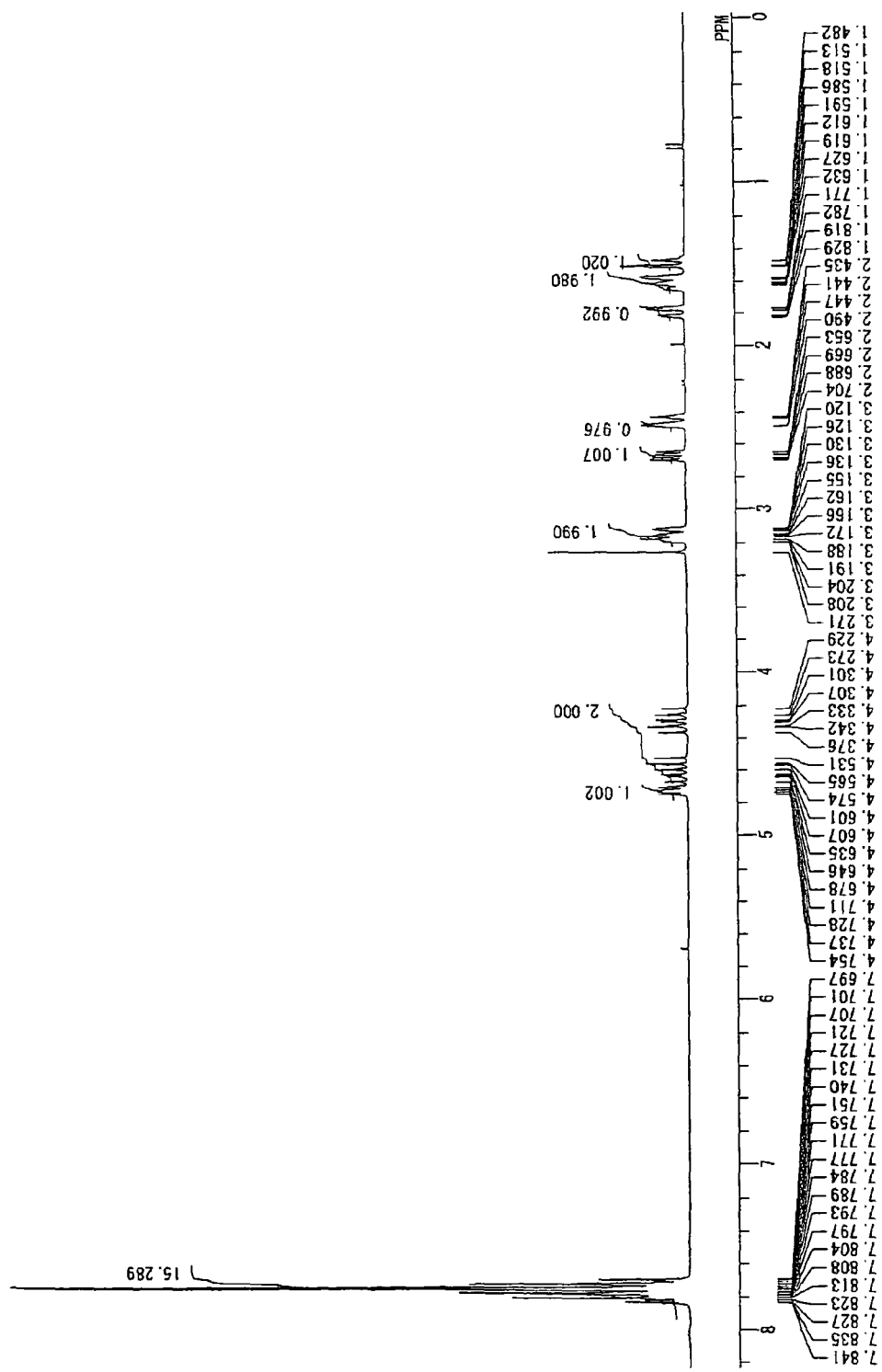
FIG. 9 is a spectrum of $^1$H-NMR/DMSO-$d_6$ of TAG4 in Synthesis Example 10.
Figure 10:
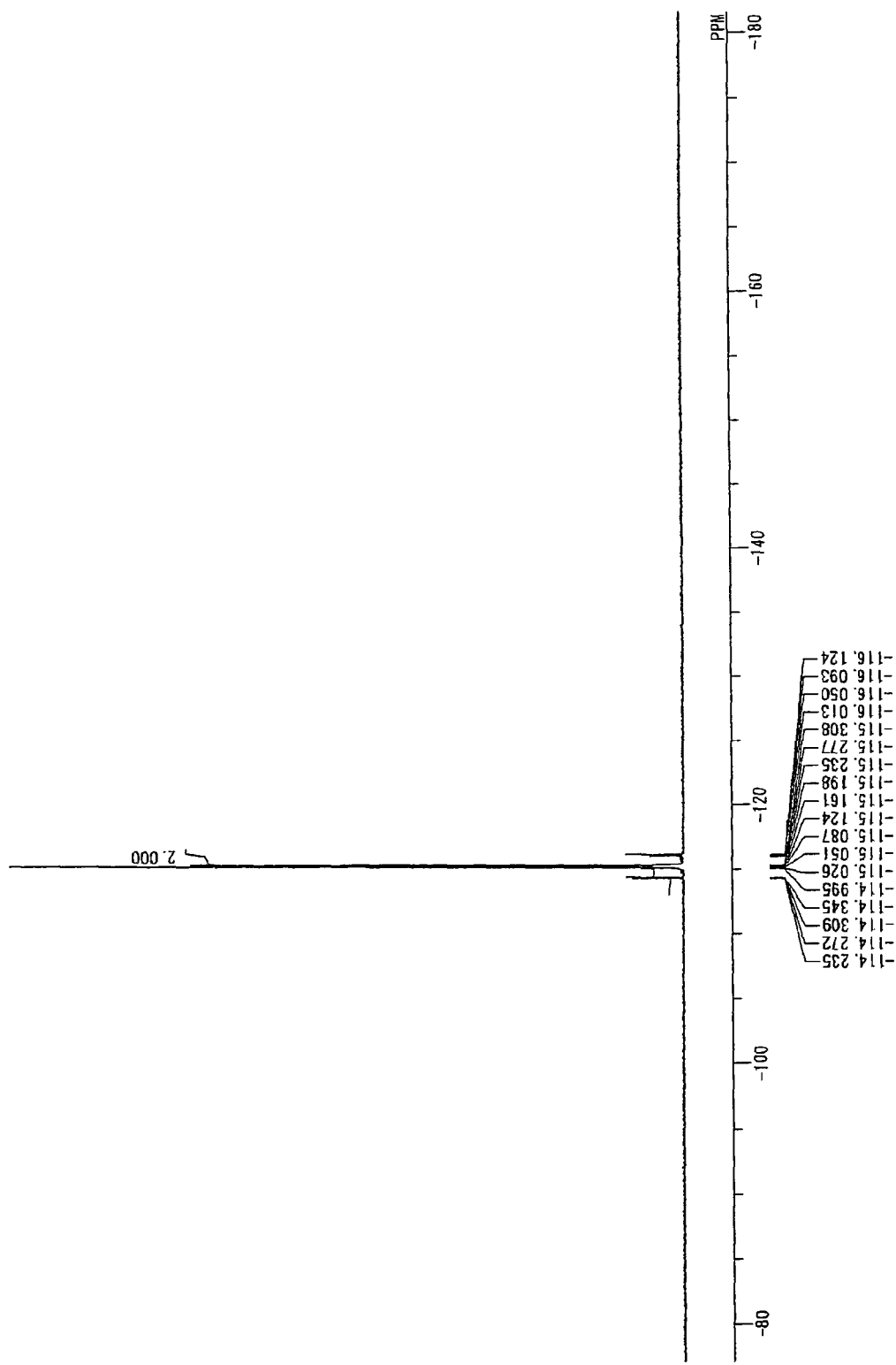
FIG. 10 is a spectrum of $^{19}$F-NMR/DMSO-$d_6$ of TAG4 in Synthesis Example 10.

After forming the resist upper layer film, exposure is conducted for a pattern circuit region 15 of the resist upper layer film (see FIG. 2(b)), post-exposure bake (PEB) is conducted preferably at 60 to 150° C., and development is conducted, according to usual manners, respectively, to obtain a resist pattern 14' (see FIG. 2(*c*)).

Next, etching is conducted by using the obtained resist pattern 14'.

Etching of the intermediate layer 13 in the three-layer resist method is conducted by a flon-based gas or the like by using the resist pattern 14' as a mask, to obtain an intermediate layer pattern 13' (see FIG. 2(*d*)). Next, dry etching mainly using an oxygen gas or the like similarly to the above-described two-layer resist method is conducted to etch the resist lower layer film 12 by using the obtained intermediate layer pattern, to obtain a resist lower layer film pattern 12' (see FIG. 2(*e*)).

Next, etching of the layer to be processed 11*b* of the substrate 11 may also be conducted according to a usual manner, exemplarily by etching mainly using a flon-based gas when the layer to be processed 1*b* of the substrate comprises a low-dielectric insulator film such as $SiO_2$, SiN, SiON, or porous silica, or by etching mainly using a chlorine-based or bromine-based gas when the layer to be processed 11*b* is poly-silicon (p-Si), Al, or W, thereby forming a pattern 11*b'* in the substrate (see FIG. 2(*f*)).

As shown in FIG. 2, the substrate 11 can be divided into the layer to be processed 11*b* to be subjected to etching, and the fundamental substrate 11*a* not to be subjected to etching, similarly to the two-layer resist method. The layer to be processed 11*b* as used may be the same as that in the two-layer resist method, and the thickness of the layer to be processed can be selected in consideration of etching conditions and the like, and preferably in a range of 0.1 to 10 μm.

Although the two-layer resist method and the three-layer resist method have been described, examples of resists each comprising four or more layers include one which comprises a typical resist as an uppermost layer, a subsequent typical antireflective film, and a subsequent silicon-containing intermediate layer, and a lowermost organic film containing no silicons. In this case, the composition of the present invention present invention can be used for the intermediate layer and lowermost layer.

EXAMPLE

Although the present invention will be concretely explained by describing Examples and Comparative Examples, the present invention is not limited by the description.

Synthesis Example 1

Synthesis of Triphenylsulfonium Chloride 40 g (0.2 mole) of diphenyl sulfoxide was dissolved in 400 g of dichloromethane, and the mixture was agitated under ice-cooling. 65 g (0.6 mole) of trimethylsilyl chloride was dropped into the mixture at a temperature not exceeding 20° C., and maturation was further conducted for 30 minutes at this temperature. Next, a Grignard reagent was dropped into the mixture at a temperature not exceeding 20° C., the Grignard reagent being separately prepared from 14.6 g (0.6 mole) of metal magnesium, 67.5 g (0.6 mole) of chlorobenzene, and 168 g of tetrahydrofuran (THF). After maturation of the reaction was conducted for 1 hour, 50 g of water was added at a temperature not exceeding 20° C. to stop the reaction, and 150 g of water, 10 g of 12N hydrochloric acid, and 200 g of diethyl ether were further added into the mixture.

Water layer was separated from the mixture, and washed by 100 g of diethyl ether, to obtain an aqueous solution of triphenylsulfonium chloride. This was not subjected to a further isolation, and the aqueous solution was directly used for the next reaction.

Synthesis Example 2

Synthesis of 4-tert-butylphenyldiphenylsulfonium bromide

The same procedure as Synthesis Example 1 was conducted, except that 4-tert-butylbromobenzene was used instead of chlorobenzene in Synthesis Example 1, and an amount of water upon extraction was increased, to obtain an intended substance.

Synthesis Example 3

Synthesis of sodium 2-(pivaloyloxy)-1,1-difluoroethanesulfonate (Anion-1)

Pivalic chloride and 2-bromo-2,2-difluoroethanol were mixed in tetrahydrofuran, and ice-cooled. Triethylamine was added into the mixture, and then a typical liquid separating operation and a distillation removal of solvent were conducted, to obtain 1-pivaloyloxy-2-bromo-2,2-difluoroethyl. Next, conversion into sodium sulfinate by sodium dithionite and oxidation by hydrogen peroxide were conducted for the mixture, to obtain intended sodium 2-(pivaloyloxy)-1,1-difluoroethanesulfonate.

Synthesis of carboxylic acid ester is known, and so is synthesis of sulfinic acid and sulfonic acid from alkyl halide. The latter is described in Japanese Patent Laid-Open (kokai) No. 2004-2252, and the like:

Synthesis Example 4

Synthesis of sodium 2-(1-adamantanecarbonyloxy)-1,1-difluoroethanesulfonate (Anion-2)

1-adamantanecarbonyl chloride and 2-bromo-2,2-difluoroethanol were mixed in tetrahydrofuran, and ice-cooled. Triethylamine was added into the mixture, and then a typical liquid separating operation and a distillation removal of solvent were conducted, to obtain 1-adamantanecarboxylic acid=2-bromo-2,2-difluoroethyl. Next, conversion into sodium sulfinate by sodium dithionite and oxidation by hydrogen peroxide were conducted for the mixture, to obtain intended sodium 2-(1-adamantanecarbonyloxy)-1,1-difluoroethanesulfonate.

Synthesis Example 5

Synthesis of triphenylsulfonium=2-(pivaloyloxy)-1,1-difluoroethanesulfonate (TAG1)

159 g (0.37 mole) of sodium 2-(pivaloyloxy)-1,1-difluoroethanesulfonate (Anion-1, purity of 63%) and the triphenylsulfonium chloride aqueous solution (0.34 mole) synthesized in Synthesis Example 1 were dissolved in 700 g of dichloromethane and 400 g of water. The organic layer separated therefrom was washed three times by 200 g of water, to condense the organic layer. Diethyl ether was added to the residue to conduct recrystallization, to obtain an intended substance as a white crystal: 164 g (yield of 95%).

Synthesis Example 6

Synthesis of triphenylsulfonium=2-(1-adamantan-ecarbonyloxy)-1,1-difluoroethanesulfonate (TAG2)

10 g (0.02 mole) of sodium 2-(1-adamantanecarbonyloxy)-1,1-difluoroethanesulfonate (Anion-2, purity of 70%) and 50 g (0.02 mole) of the triphenylsulfonium chloride aqueous solution synthesized in Synthesis Example 1 were dissolved in 100 g of dichloromethane. The organic layer separated therefrom was washed three times by 20 g of water, to condense the organic layer. Diethyl ether was added to the residue to conduct recrystallization, to obtain an intended substance as a white crystal: 10 g (yield of 85%).

Synthesis Example 7

Synthesis of 4-tert-butylphenyldiphenylsulfonium=2-(pivaloyloxy)-1,1-difluoroethanesulfonate (TAG5)

20 g (0.052 mole) of sodium 2-(pivaloyloxy)-1,1-difluoroethanesulfonate (Anion-1, purity of 70%) and 217 g (0.052 mole) of the 4-tert-butylphenyldiphenylsulfonium bromide aqueous solution synthesized in Synthesis Example 2 were dissolved in 150 g of dichloromethane. The organic layer separated therefrom was washed three times by 50 g of water, to condense the organic layer. Diethyl ether was added to the residue to conduct recrystallization, to obtain an intended substance as a white crystal: 26 g (yield of 79%).

Synthesis Example 8

Synthesis of triphenylsulfonium=1,1-difluoro-2-hydroxyethanesulfonate (Alkaline hydrolysis of TAG1; TAG intermediate product 1)

243.5 g (0.48 mole) of triphenylsulfonium=2-(pivaloyloxy)-1,1-difluoroethanesulfonate (TAG1) was dissolved in 760 g of methanol, and ice-cooled. Dropped into the mixture was sodium hydroxide aqueous solution [prepared by dissolving 40 g of sodium hydroxide in 120 g of water], at a temperature not exceeding 5° C. Maturation was conducted at a room temperature for 8 hours, and dilute hydrochloric acid (99.8 g of 12N hydrochloric acid, and 200 g of water) was added to the mixture at a temperature not exceeding 10° C. to stop the reaction, and the methanol was removed under reduced pressure. 1,000 g of dichloromethane was added to the mixture, the organic layer was washed by 30 g of saturated saline solution three times, and then the organic layer was concentrated, followed by addition of 1 L of diisopropyl ether to the residue to crystallize it. The thus obtained crystal was filtered and dried, to obtain an intended substance: 187 g (purity of 78%, and converted yield of 78%).

Synthesis Example 9

Synthesis of triphenylsulfonium=1,1-difluoro-2-hydroxyethanesulfonate (Alkaline Hydrolysis of TAG1; TAG Intermediate Product 2)

50.9 g (0.1 mole) of triphenylsulfonium=2-(pivaloyloxy)-1,1-difluoroethanesulfonate (TAG1) was dissolved in 200 g of methanol, and ice-cooled. 2.0 g of 28 mass % sodium methoxide/methanol solution was added to the mixture, maturation was then conducted at a room temperature for 24 hours, 1.0 g of 12N hydrochloric acid was added to the mixture at a temperature not exceeding 10° C. to stop the reaction, and the methanol was removed under reduced pressure. 250 g of dichloromethane was added to the mixture, and inorganic salts were filtered out, the filtrate was thereafter concentrated, and 150 g of diisopropyl ether was added to the residue to crystallize it. The thus obtained crystal was filtered and dried, to obtain an intended substance: 42 g (purity of 99%, and converted yield of 99%).

Synthesis Example 10

Synthesis of triphenylsulfonium 4-oxo-5-oxatricyclo[4.2.1.0$^{3,7}$]nonane-2-carboxylic acid=1-difluorosulfomethyl-2,2,2-trifluoroethyl (Reacylation of TAG Intermediate Product; TAG4)

5.7 g (0.01 mole) of triphenylsulfonium=1,1-difluoro-2-hydroxyethanesulfonate (purity of 74.4%) obtained in the same procedure as Synthesis Example 8, and 1.2 g (0.012 mole) of triethylamine, 0.12 g (0.001 mole) of N,N-dimethylaminopyridine were dissolved into 20 g of acetonitrile and 20 g of dichloromethane, and ice-cooled. 2.2 g (0.012 mole) of 4-oxo-5-oxatricyclo[4.2.1.0$^{3,7}$]nonane-2-carboxylic acid chloride was added to the mixture at a temperature not exceeding 5° C., followed by agitation at a room temperature for one hour. Dilute hydrochloric acid aqueous solution prepared from 2 g of 12N hydrochloric acid and 10 g of water was added to the mixture, and then the solvent was distilledly removed under reduced pressure. 50 g of dichloromethane, 25 g of methyl isobutyl ketone, and 20 g of water were added to the residue, the organic layer was separated therefrom, and this organic layer was then washed by 20 g of water and the solvent was distilledly removed under reduced pressure. Ether was added to the residue to conduct crystallization, followed by filtering and drying, to obtain 4.6 g of an intended substance (yield of 78%).

TAG1 to TAG4 obtained in the above have structural formulae shown below, respectively:

[TAG 1]

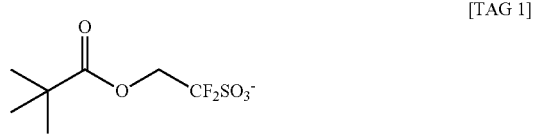

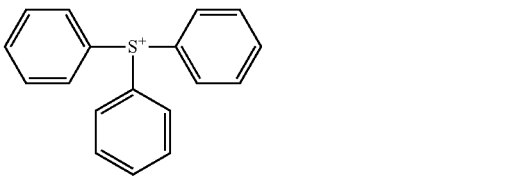

[TAG 2]

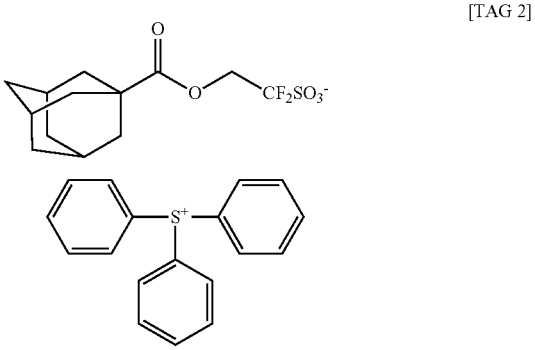

-continued

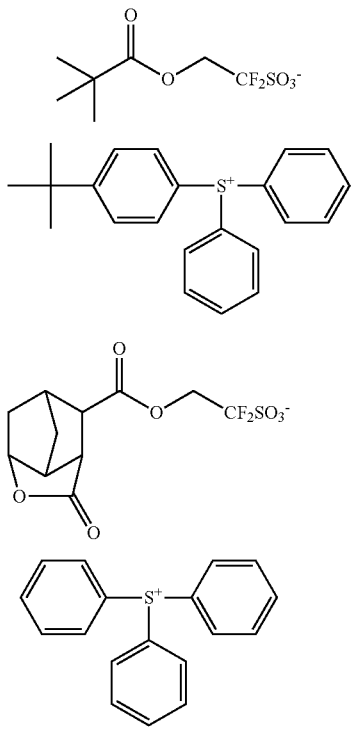

[TAG 3]

[TAG 4]

Further, nuclear magnetic resonance spectra (1H-NMR, $^{19}$F-NMR) of these (TAG1) to (TAG4) are shown in FIG. 3 to FIG. 10, respectively.

Note that although 4-oxo-5-oxatricyclo[4.2.1.0$^{3,7}$]nonane-2-carbonyloxy group in an anion moiety of TAG4 has one endo-/exo-portion, the thermal acid generator of the present invention may be constituted of a single compound only, or a mixture of isomers.

As seen from the results of the nuclear magnetic resonance spectra, the acid generator for generating the acid represented by the general formula (1) contained in the resist lower-layer composition of the present invention was allowed to be synthesized by using the industrially available 2-bromo-2,2-difluoroethanol used in Synthesis Example 3 and Synthesis Example 4, as a starting material. Further, as seen from the case of Synthesis Example 10 (TAG4), it was possible to introduce a polar substitutional group such as lactone into the acid generator, by using an intermediate product after alkaline hydrolysis.

Synthesis Example 11

Synthesis of triethylammonium=1,1-difluoro-2-(pivaloyloxy)ethanesulfonate (TAG5)

Triethylamine was dissolved in cold water, hydrochloric acid was added thereto, and then sodium 2-(pivaloyloxy)-1,1-difluoroethanesulfonate (Anion-1) in Synthesis Example 3 and dichloromethane were added to the mixture, followed by agitation. The organic layer separated therefrom was washed by water, and dichloromethane was distilledly removed under reduced pressure from the organic layer after washing. The intended substance was obtained as an oily substance at a yield of 69%. The spectra data of the obtained intended substance are shown below.

Nuclear Magnetic Resonance Spectrum ($^1$H-NMR/ DMSO-d$_6$; 300 MHz):
8.80 (1H, (b), NH$^+$), 4.52-4.58 (2H, (t), OCH$_2$CF$_2$), 3.06-3.12 (6H, (q), CH$_2$CH$_3$), 1.14-1.19 (9H, (t), CH$_2$CH$_3$), 1.16 (9H, (s), C(CH$_3$)$_3$)

Nuclear Magnetic Resonance Spectrum ($^{19}$F-NMR/ DMSO-d$_6$; 300 MHz):
−115.83 to −115.72 (2F, (t), CF$_2$)

Infrared Absorption Spectrum (IR(KBr); cm$^{-1}$):
3043, 2979, 2875, 2817, 2744, 1743, 1481, 1400, 1280, 1222, 1149, 1130, 1106, 1031, 1014, 981, 952, 646

Time of Flight Mass Spectrometry (TOFMS; MALDI):
POSITIVE M$^+$102 (corresponding to (C$_2$H$_5$)$_3$NH$^+$)
NEGATIVE M$^-$245 (corresponding to (CH$_3$)$_3$CCOOCH$_2$OF$_2$SO$_3^-$)

Synthesis Example 12

Synthesis of tetrabutylammonium=1,1-difluoro-2-(pivaloyloxy)ethanesulfonate (TAG6)

Commercially available tetra-n-butylammonium hydrogen sulfate, sodium 2-(pivaloyloxy)-1,1-difluoroethanesulfonate (Anion-1) of Synthesis Example 3, and dichloromethane were added to one another, followed by agitation. The organic layer separated therefrom was washed by water, and dichloromethane was distilledly removed under reduced pressure from the organic layer after washing. The intended substance was obtained as an oily substance at a yield of 81%. The spectra data of the obtained intended substance are shown below.

Nuclear Magnetic Resonance Spectrum ($^1$H-NMR/ DMSO-d$_6$; 300 MHz):
4.47-4.57 (2H, (t), CH$_2$), 3.13-3.18 (8H, (m), CH$_2$), 1.51-1.61 (8H, (m), CH$_2$), 1.24-1.36 (8H, (m), CH$_2$) 1.16 (9H, (s), C(CH$_3$)$_3$), 0.90-0.95 (12H, (t), CH$_2$CH$_3$)

Nuclear Magnetic Resonance Spectrum ($^{19}$F-NMR/ DMSO-d$_6$; 300 MHz):
−115.87 to −115.76 (2F, (t), CF$_2$)

Infrared Absorption Spectrum (IR(KBr); cm$^{-1}$):
2964, 2877, 1739, 1481, 1257, 1238, 1149, 1126, 1105, 1014, 979, 644

Time of Flight Mass Spectrometry (TOFMS; MALDI):
POSITIVE M$^+$242 (corresponding to (C$_4$H$_9$)$_4$N$^+$)
NEGATIVE M$^-$245 (corresponding to (CH$_3$)$_3$CCOOCH$_2$CF$_2$SO$_3^-$)

Synthesis Example 13

Synthesis of benzyltrimethylammonium=1,1-difluoro-2-(pivaloyloxy)ethanesulfonate (TAG7)

Commercially available benzyltrimethylammonium chloride, sodium 2-(pivaloyloxy)-1,1-difluoroethanesulfonate (Anion-1) of Synthesis Example 3, and dichloromethane were added to one another, followed by agitation. The organic layer separated therefrom was washed by water, and dichloromethane was distilledly removed under reduced pressure from the organic layer after washing. Diisopropyl ether was added to the residue to conduct crystallization, followed by filtering and drying, to obtain an intended substance at a yield of 98%. The spectra data of the obtained intended substance are shown below.

Nuclear Magnetic Resonance Spectrum ($^1$H-NMR/ DMSO-d$_6$; 300 MHz):
7.53 (5H, (s), Ph-H), 4.48-4.59 (2H, (t), CH$_2$), 4.51 (2H, (s), CH$_2$), 3.01 (9H, (s), CH$_3$), 1.16 (9H, (s), C(CH$_3$)$_3$)

Nuclear Magnetic Resonance Spectrum ($^{19}$F-NMR/DMSO-$d_6$; 300 MHz):

−115.76 to −115.65 (2F, (t), $CF_2$)

Infrared Absorption Spectrum (IR(KBr); cm$^{-1}$):

2943, 1743, 1494, 1483, 1238, 1151, 1128, 1016, 977, 892, 781, 728, 703, 647

Time of Flight Mass Spectrometry (TOFMS; MALDI):

POSITIVE M$^+$145 (corresponding to $C_6H_5CH_2N^+(CH_3)_3$)

NEGATIVE M$^-$245 (corresponding to $(CH_3)_3CCOOCH_2CF_2SO_3^-$)

TAG5 to TAG7 obtained in the above have structural formulae shown below, respectively:

[TAG 5]
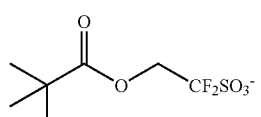
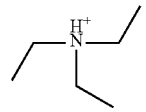

[TAG 6]
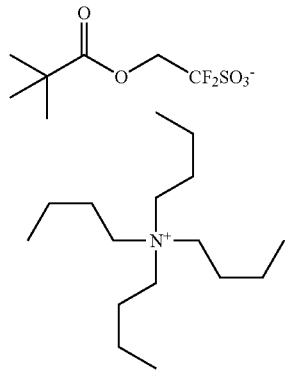

[TAG 7]
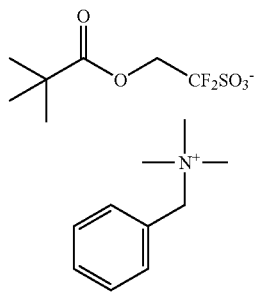

Examples 1 to 9, and Comparative Examples 1 and 2

As shown in Table 1, dissolved in solvents were resins represented by Polymers 1 to 8, thermal acid generators represented by TAG5 to TAG7 synthesized in the above Synthesis Examples or represented by RFPAG1, RFPAG2, and acid crosslinking agents represented by CR1, CR2, followed by filtration by a filter made of 0.1 fluororesin, thereby preparing resist lower layer film solutions (Examples 1 to 7, and Comparative Example 1), and silicon-containing intermediate layer solutions (Examples 8, 9, and Comparative Example 2), respectively: Some of the polymers were occasionally obtained as a propylene glycol monomethyl ether acetate solution, and in such cases, the polymers were calculated as solid matters to prepare the composition solutions listed in Table 1, respectively. Note that lower layer films and intermediate layers formed by process to be described later are named UDL1 to 7, SOG1 and 2, Comparative Example UDL1, and Comparative Example SOG1, respectively.

TABLE 1

| | Polymer (parts by mass) | Crosslinking agent (parts by mass) | Acid generator (parts by mass) | Solvent (parts by mass) | Name of formed film |
|---|---|---|---|---|---|
| Example 1 | Polymer 1 (28.0) | CR 1 (10.0) | TAG 5 (1.0) | PGMEA (100) | UDL1 |
| Example 2 | Polymer 1 (28.0) | CR 1 (10.0) | TAG 7 (1.0) | PGMEA (100) | UDL2 |
| Example 3 | Polymer 2 (28.0) | CR 1 (10.0) | TAG 5 (1.0) | PGMEA (100) | UDL3 |
| Example 4 | Polymer 3 (28.0) | CR 2 (10.0) | TAG 6 (1.0) | PGMEA (100) | UDL4 |
| Example 5 | Polymer 4 (28.0) | CR 1 (10.0) | TAG 5 (1.0) | PGMEA (100) | UDL5 |
| Example 6 | Polymer 4 (28.0) | CR 1 (10.0) | TAG 7 (1.0) | PGMEA (100) | UDL6 |
| Example 7 | Polymer 5 (28.0) | CR 1 (10.0) | TAG 5 (1.0) | PGMEA (100) | UDL7 |
| Example 8 | Polymer 6 (28.0) | — | TAG 5 (1.0) | PGMEA (100) | SOG1 |
| Example 9 | Polymer 7 (28.0) | — | TAG 7 (1.0) | PGMEA (100) | SOG2 |
| Comparative Example 1 | Polymer 1 (28.0) | CR 1 (10.0) | RFPAG 1 (1.0) | PGMEA (100) | Comparative Example UDL1 |
| Comparative Example 2 | Polymer 6 (28.0) | — | RFPAG 2 (1.0) | PGMEA (100) | Comparative Example SOG1 |

Compounds represented by abbreviations in Table 1 are as follows:

Polymer 1

Cocondensation novolak resin of m-cresol and 1-naphthol cocondensed by formaldehyde (ratio of m-cresol:1-naphthol=80:20, Mw=14,000, Mw/Mn=3.6)

Polymer 2

Novolak resin of 4,4'-(9H-fluorene-9-ylidene)bisphenol condensed by formaldehyde (Mw=16,000; Mw/Mn=4.3)

Polymer 3

Copolymerization resin of indene and 4-hydroxystyrene (indene: 4-hydroxystyrene=70:30, Mw=14,000, Mw/Mn=1.7)

Polymer 4

Cocondensation novolak resin of 1-naphthol and dicyclopentadiene (ratio of 1-naphthol:dicyclopentadiene=70:30, Mw=1,200, Mw/Mn=2.8)

Polymer 5

Copolymerization resin of acenaphthylene and 4-hydroxystyrene (acenaphthylene: 4-hydroxystyrene=70:30, Mw=3,500, Mw/Mn=1.66)

Polymer 6

Polymer prepared from 139 g of 2-(3,4-epoxycyclohexyl) ethyltrimethoxysilane: 32 g of phenyltrimethoxysilane (compound of Synthesis Example 2 described in Japanese Patent Laid-Open (kokai) No. 2005-18054)

Polymer 7

Polymer prepared from 24.6 g of 2-(3,4-epoxycyclohexyl) ethyltrimethoxysilane: 19.8 g of phenyltrimethoxysilane: 28.6 g of spiro[2-oxooxolane-3,5'-bicyclo[2.2.1]heptanetrimethoxysilane], Mw=2,300 (compound of Synthesis Example 8 described in Japanese Patent Laid-Open (kokai) No. 2004-310019)

RFPAG1 tetrabutylammonium trifluoromethanesulfonate

RFPAG2 bis(4-tert-butylphenyl)iodonium nonafluoro-1-butanesulfonate

CR1

1,3,4,6-tetrakis(methoxymethyl)glycoluril

CR2 o-cresylglycidyl ether: formaldehyde copolymer (manufactured by Sigma-Aldrich Corporation)

PGMEA

Solution provided by dissolving 0.01 wt % of the following surfactant A in 100 wt % of propylene glycol monomethyl ether acetate Surfactant A:

3-methyl-3-(2,2,2-trifluoroethoxymethyl)oxetane: tetrahydrofuran: 2,2-dimethyl-1,3-propane diol copolymer (manufactured by Omnova Solutions Inc.) (structural formula is shown below)

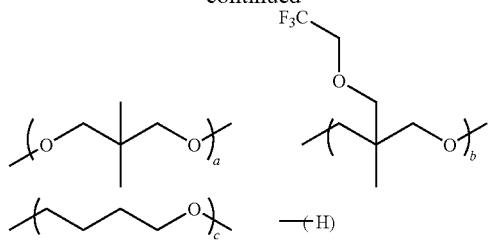

$a:(b+b'):(c+c')=1:4$ to $7:0.01$ to $1$ (molar ratio); weight-average molecular weight 1,500

(Arf Resist 1 to 3)

Next, resist upper layer film solutions (ArF resists 1 to 3) were prepared by dissolution of resist compositions listed in Table 2, followed by filtration by a filter made of 0.1 μm fluororesin.

TABLE 2

| | Polymer (parts by mass) | Acid generator (parts by mass) | Sensitivity adjuster (parts by mass) | Solvent (parts by mass) |
|---|---|---|---|---|
| ArF resist 1 | ArF polymer 1 (100) | TAG 1 (2.2) | BASE 1 (0.3) | PGMEA (1,200) |
| ArF resist 2 | ArF polymer 1 (100) | TAG 2 (2.2) | BASE 1 (0.3) | PGMEA (1,200) |
| ArF resist 3 | ArF polymer 2 (100) | RFPAG 3 (2.2) | BASE 1 (0.3) | PGMEA (1,200) |

Compounds represented by abbreviations in Table 2 are as follows:

ArF polymer 1 poly(5-oxo-4,8-dioxatricyclo[4.2.1.0$^{3,7}$]nona-2-yl methacrylate: 3-hydroxy-1-adamantyl methacrylate: 2-ethyl-2-adamantyl methacrylate)

Molar ratio=0.40:0.30:0.30

Weight-average molecular weight=7,800

ArF polymer 2

5 or 6-(trimethoxysilyl)bicyclo[2.2.1]heptane-2-carboxylicacid=1-ethylcyclopentyl: 1,1-bis-(trifluoromethyl)-2-(5 or 6-(trimethoxysilyl)bicyclo[2.2.1]heptane-2-yl)ethanol: or 6-(trimethoxysilyl)spiro[bicyclo[2.2.1]heptane-2,3'(2'H)-furan]-5'(4'H)-one polycondensate (described in Japanese Patent Laid-Open (kokai) No. 2006-106311)

Molar ratio=0.25:0.20:0.55

Weight-average molecular weight=3,300

RFPAG3 triphenylsulfonium nonafluoro-1-butanesulfonate

BASE1 tris(2-methoxymethoxyethyl)amine

PGMEA

Identical to Table 1

Observation of Resist Pattern Profile on Low-Dielectric Insulator Substrate After Development Examples 10 to 18, Comparative Example 3

Porous silica LK-0001 manufactured by Shin-Etsu Chemical Co., Ltd. was spin coated onto silicon substrates, followed by baking at 400° C. for 60 seconds, to obtain low-dielectric insulator films each having a specific dielectric constant of 2.5. The low-dielectric insulator substrates were immersed into a triethylamine solution, followed by heating at 80° C. for 10 minutes, to adsorb amine components to the low-dielectric films.

Duly coated onto the low-dielectric insulator substrates having amine components adsorbed thereon by the above procedure, were the above prepared resist lower layer film solutions of Examples 1 to 7, and Comparative Example 1, followed by baking at 220° C. for 60 seconds, to form resist lower layer films having thicknesses of 200 nm, respectively.

lowed by baking (PEB) at 110° C. for 60 seconds and by development by a 2.38 mass % tetramethylammonium hydroxide (TMAH) aqueous solution for 60 seconds, to form a positive pattern of 75 nm L/S (line and space). Listed in Table 3 together with the previous composition combinations, are results of observation of the obtained resist cross-sectional pattern profiles by an electron microscope (S-4700) manufactured by Hitachi, Ltd.

TABLE 3

|  | Lower layer film | Intermediate layer film (SOG) | Resist layer | Resist pattern profile after development | Wafer abbreviation |
|---|---|---|---|---|---|
| Example 10 | UDL1 | SOG1 | ArF resist 1 | Rectangular | Tri1 |
| Example 11 | UDL4 | SOG1 | ArF resist 1 | Rectangular | Tri2 |
| Example 12 | UDL3 | SOG2 | ArF resist 2 | Rectangular | Tri3 |
| Example 13 | UDL2 | — | ArF resist 3 | Rectangular | Bi1 |
| Example 14 | UDL5 | SOG1 | ArF resist 2 | Rectangular | Tri4 |
| Example 15 | UDL6 | SOG1 | ArF resist 1 | Rectangular | Tri5 |
| Example 16 | UDL7 | Comparative Example SOG1 | ArF resist 2 | Rectangular | Tri6 |
| Example 17 | UDL6 | — | ArF resist 3 | Rectangular | Bi2 |
| Example 18 | UDL1 | SOG2 | ArF resist 2 | Rectangular | Tri7 |
| Comparative Example 3 | Comparative Example UDL1 | Comparative Example SOG1 | ArF resist 1 | Slight footing | Comparative Example Tri1 |

As noted above, the laminated resist lower layer films were called UDL1 to 7, and Comparative Example UDL1, respectively.

Next, the above prepared intermediate layer solutions of Examples 8, 9, and Comparative Example 2 were duly coated onto applicable ones of UDL1 to 7, and Comparative Example UDL1, followed by baking at 200° C. for 60 seconds, to form intermediate-layered films having thicknesses of 70 nm, respectively. Note that the intermediate layers laminated based on Examples 8, 9, and Comparative Example 2 were called SOG1, 2, and Comparative Example SOG1, respectively, as mentioned above.

The ArF resist 1 and 2 as the above prepared solutions of the resist upper layer films were coated onto those substrates formed with the resist lower layer film and intermediate layer, respectively, followed by baking at 120° C. for 60 seconds, to form resist upper layer films having thicknesses of 180 nm, respectively (Examples 10 to 12, 14 to 16, 18, and Comparative Example 3).

In turn, the ArF resist 3 as a solution of upper layer film composition of two-layer resist was coated onto the applicable resist lower layer films (UDL2, and UDL6), followed by baking at 120° C. for 60 seconds, to form resist upper layer films of two-layer resists, having thicknesses of 130 nm, respectively (Examples 13 and 17).

These combinations of resist lower layer films, intermediate layers, and resist upper layer' films are listed in Table 3. Wafer abbreviations of the laminated combinations of are represented as Tri-1 to 7, Bi-1 and 2, and Comparative Example Tri-1, respectively.

Next, exposure was conducted by an ArF exposure system (S307E manufactured by Nikon Corp., NA=0.85, σ=0.93, 4/5 annular illumination, 6% halftone phase-shift mask), fol- As a result, it was confirmed that, in case of adoption of the resist lower layer film compositions of Examples 10 to 18, no affections from amine-contaminated underlying substrates were found near interfaces between resist upper layer films and underlying layers, and thus profile changes due to footing, undercut, and the like were not caused, to obtain rectangular patterns, respectively.

Observation of Resist Pattern Profile on SiN Substrate

Examples 19 to 27, Comparative Example 4

SiN films having thicknesses of 100 nm were formed on silicon substrates by a CVD method, respectively. Resist lower layer films, intermediate layers, and resist upper layer films were formed in the same manner as Tri-1 to 7, Bi-1, 2, and Comparative Example Tri-1, respectively, and pattern formation was conducted, followed by similar observation of resist pattern profiles. Identically to the above, the systems adopting the resist lower-layer compositions of the present invention exhibited rectangular profiles, and the composition of the Comparative Example exhibited a slight footing in profile.

Measurement of Airborne Particle

Examples 28 to 34, and Comparative Example 5

The resist lower layer film compositions (Examples 1 to 7, and Comparative Example 1) were coated onto silicon substrates having SiO$_2$ of 300 nm thickness laminated thereon, followed by baking at 220° C. for 60-seconds, to obtain resist lower layer films having thicknesses of 300 nm, respectively. For coating and baking operations, and for a developing operation to be described later, Coater/Developer Clean Track Act 8 manufactured by Tokyo Electron Limited was used.

Here, the numbers of airborne particles of 0.30 (diameter) within the apparatus of Clean Track Act 8 were continuously measured by KR-11A airborne particle counter manufactured by Rion Co., Ltd., and the results thereof are shown in Table 4. The lower layer film compositions of Examples 1 to 7 (resist lower layer film names: UDL1 to 7) exhibited maximum values of 10 to 10,000/L, and Comparative Example 1 (resist lower layer film name: Comparative Example UDL1) exhibited a maximum value of 400,000/L or more, thereby suggesting that volatile components to be counted as airborne particles were decreased in case of the compositions of the present invention.

TABLE 4

|  | Name of formed film | Numbers of airborne particle (maximum value/L) |
|---|---|---|
| Example 28 | UDL1 | 10000 |
| Example 29 | UDL2 | 10 |
| Example 30 | UDL3 | 100 |
| Example 31 | UDL4 | 5000 |
| Example 32 | UDL5 | 9000 |
| Example 33 | UDL6 | 50 |
| Example 34 | UDL7 | 10 |
| Comparative Example 5 | Comparative Example UDL1 | 400000 |

Pattern Formation

Examples 35 to 43, and Comparative Example 6

Transference of the resist patterns obtained in Examples 10 to 18, and Comparative Example 3 to silicon-containing intermediate layer and/or resist lower layer film can be conducted under a typical etching condition.

More concretely, transference of resist patterns containing no silicon atoms (Examples 10 to 12, 14 to 16, 18, and Comparative Example 3; wafer abbreviations Tri-1 to 17, Comparative Example Tri-1) to silicon-containing intermediate layers (SOG films) was conducted by a dry etching apparatus TE-8500P manufactured by Tokyo Electron Limited. Etching conditions are as follows.

| Chamber pressure: | 40.0 Pa |
|---|---|
| RF power: | 1,000 W |
| Gap: | 9 mm |
| CHF$_3$ gas flow rate: | 20 ml/min |
| CF$_4$ gas flow rate: | 60 ml/min |
| Ar gas flow rate: | 200 ml/min |
| Time: | 30 sec |

Next, the patterns transferred to the SOG films or resist patterns including silicon atoms (two-layer films represented by Examples 13 and 17: wafer abbreviations Bi-1 and 2) were transferred to the lower layer films, by the following etching mainly using an oxygen gas. Etching conditions are as follows.

| Chamber pressure: | 60.0 Pa |
|---|---|
| RF power: | 600 W |

-continued

| Ar gas flow rate: | 40 ml/min |
|---|---|
| O$_2$ gas flow rate: | 60 ml/min |
| Gap: | 9 mm |
| Time: | 20 sec |

Finally, the substrates to be processed were processed by using the resist lower layer film patterns as masks, respectively. Etching conditions are as follows.

| Chamber pressure: | 40.0 Pa |
|---|---|
| RF power: | 1,300 W |
| Gap: | 9 mm |
| CHF$_3$ gas flow rate: | 30 ml/min |
| CF$_4$ gas flow rate: | 30 ml/min |
| Ar gas flow rate: | 100 ml/min |
| Time: | 60 sec |

When pattern cross sections were observed by a scanning electron microscope (S-4700) manufactured by Hitachi, Ltd., it was confirmed that the profiles were also excellent after fluorine-based etching (intermediate-layered film etching), after oxygen etching (lower layer film etching), and after etching the substrates to be processed (SiO$_2$ substrate etching). The results are shown in Table 5.

TABLE 5

|  | Wafer abbreviation | Profile after intermediate layer etching | Profile after lower layer film etching | Profile after SiO$_2$ substrate etching |
|---|---|---|---|---|
| Example 35 | Tri1 | Rectangular | Rectangular | Rectangular |
| Example 36 | Tri2 | Rectangular | Rectangular | Rectangular |
| Example 37 | Tri3 | Rectangular | Rectangular | Rectangular |
| Example 38 | Bi1 | — | Rectangular | Rectangular |
| Example 39 | Tri4 | Rectangular | Rectangular | Rectangular |
| Example 40 | Tri5 | Rectangular | Rectangular | Rectangular |
| Example 41 | Tri6 | Rectangular | Rectangular | Rectangular |
| Example 42 | Bi2 | — | Rectangular | Rectangular |
| Example 43 | Tri7 | Rectangular | Rectangular | Rectangular |
| Comparative Example 6 | Comparative Example Tri1 | Slight footing | Slight footing | Slight footing |

As described above, the resist lower-layer compositions of the present invention restrict expression of airborne particles within a coater, i.e., are low in volatility as shown in Table 4, and are excellent (rectangular, i.e., vertically profiled) in resist pattern profile after development and in pattern profile of intermediate layer, lower layer film, and substrate as underlying layers after etching thereof as shown in Table 3 and Table 5, respectively. Moreover, since the resist lower-layer compositions each include an, ester in a molecule as shown in Synthesis Example 8 and Synthesis Example 9, alkaline hydrolysis is easily progressed and thus the compositions can be quickly hydrolyzed upon waste liquid treatment, thereby allowing expectation of absence of environment load unlike indecomposable perfluoroalkanesulfonic acids.

What is claimed is:
1. A resist lower-layer composition configured to be used by a multi-layer resist method used in lithography to form a layer lower than a photoresist layer acting as a resist upper layer film, wherein
the lower layer obtained by coating and baking the resist lower-layer composition is insoluble or poorly-soluble in an alkaline developer, and
wherein the resist lower-layer composition comprises, at least, a thermal acid generator represented by the general formula (3) for generating an acid represented by the general formula (1) by heating at a temperature of 100° C. or higher:

 (1)

wherein, R represents any one of methyl group, ethyl group, n-propyl group, sec-propyl group, cyclopropyl group, n-butyl group, sec-butyl group, iso-butyl group, tert-butyl group, n-pentyl group, cyclopentyl group, n-hexyl group, cyclohexyl group, n-octyl group, n-decyl group, n-dodecyl group, 1-adamantyl group, 2-adamantyl group, bicycle[2.2.1]hepten-2-yl group, phenyl group, 4-methoxyphenyl group, 4-tert-butylphenyl group, 4-biphenyl group, 1-naphthyl group, 2-naphthyl group, 10-anthranyl group, 2-furanyl group, 4-oxo-cyclohexyl group, and following groups:

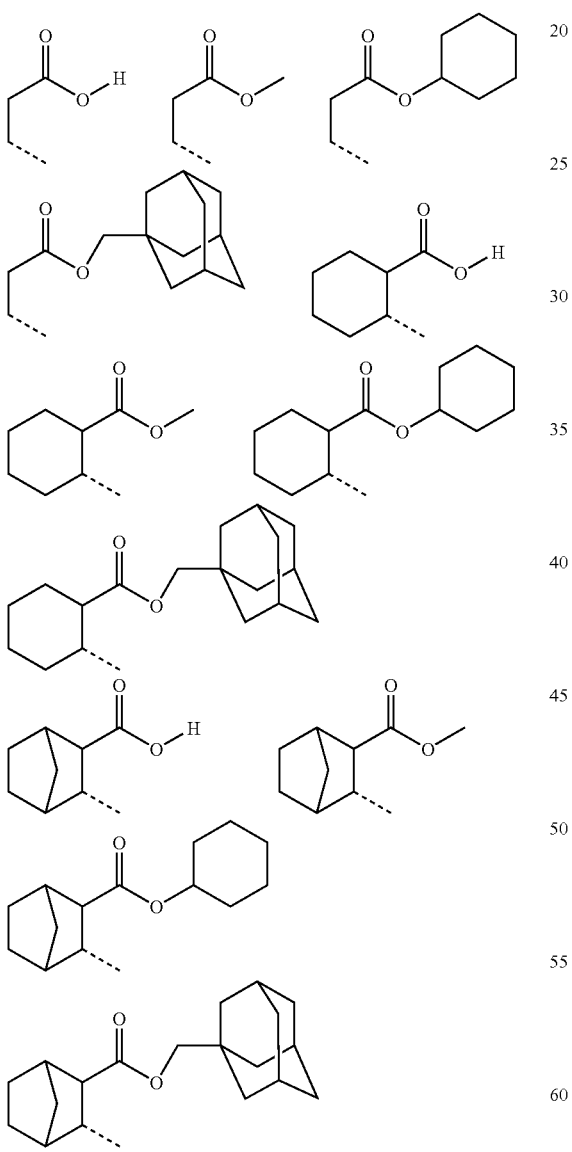

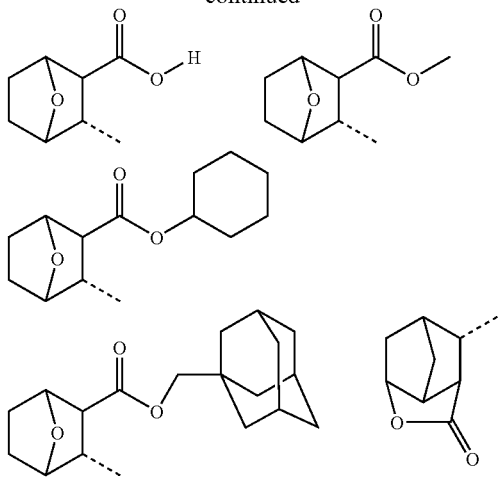

wherein, a broken line in the formula represents a bond hands,

 (3)

wherein, R represents the same meaning as before; and R¹'s mutually independently represent a hydrogen atom, a substituted or unsubstituted linear, branched, or cyclic alkyl group, alkenyl group, or oxoalkyl group having 1 to 10 carbon atoms, or a substituted or unsubstituted aryl group, aralkyl group, or aryloxoalkyl group having 6 to 18 carbon atoms, or alternatively, two or more of R¹'s may be mutually bonded to form a ring together with N in the formula.

2. The resist lower-layer composition according to claim 1, wherein the resist lower-layer composition further comprises a base resin and an acid crosslinking agent.

3. The resist lower-layer composition according to claim 2, wherein the base resin of the resist lower-layer composition has an acid-crosslinking property.

4. The resist lower-layer composition according to claim 2, wherein the base resin of the resist lower-layer composition contains a silicon atom.

5. The resist lower-layer composition according to claim 2, wherein the base resin of the resist lower-layer composition contains none of a silicon atom, titanium atom, and germanium atom, but contains carbons in an amount of 50 mass % or more.

6. The resist lower-layer composition according to claim 1, wherein the resist lower-layer composition further comprises an organic solvent.

7. A substrate including a layer to be processed, wherein the substrate comprises, at least, a resist lower layer film formed by using the resist lower-layer composition according to claim 1, on the layer to be processed.

8. The substrate according to claim 7, wherein the layer to be processed of the substrate is a low-dielectric film having a specific dielectric constant of 3.5 or less or a nitride film.

* * * * *